US008377990B2

(12) United States Patent
Nudelman et al.

(10) Patent No.: US 8,377,990 B2
(45) Date of Patent: Feb. 19, 2013

(54) CONJUGATES COMPRISING A PSYCHOTROPIC DRUG OR A GABA AGONIST AND AN ORGANIC ACID AND THEIR USE IN TREATING PAIN AND OTHER CNS DISORDERS

(75) Inventors: Abraham Nudelman, Rechovot (IL); Ada Rephaeli, Herzlia (IL); Irit Gil-Ad, Herzlia (IL); Abraham Weizman, Tel-Aviv (IL)

(73) Assignees: Ramot at Tel-Aviv University Ltd., Tel-Aviv (IL); Bar-Ilan University, Ramat-Gan (IL)

( * ) Notice: Subject to any disclaimer, the term of this patent is extended or adjusted under 35 U.S.C. 154(b) by 600 days.

(21) Appl. No.: 12/309,361

(22) PCT Filed: Jul. 17, 2007

(86) PCT No.: PCT/IL2007/000903
§ 371 (c)(1),
(2), (4) Date: Feb. 12, 2010

(87) PCT Pub. No.: WO2008/010223
PCT Pub. Date: Jan. 24, 2008

(65) Prior Publication Data
US 2010/0144869 A1 Jun. 10, 2010

Related U.S. Application Data

(60) Provisional application No. 60/831,192, filed on Jul. 17, 2006, provisional application No. 60/831,195, filed on Jul. 17, 2006.

(51) Int. Cl.
*A01N 37/18* (2006.01)
*A61K 31/16* (2006.01)
*C07C 233/00* (2006.01)
*C07C 235/00* (2006.01)
*C07C 237/00* (2006.01)
*C07C 239/00* (2006.01)

(52) U.S. Cl. ........................................ 514/630; 564/219
(58) Field of Classification Search .................. 514/630; 564/219
See application file for complete search history.

(56) References Cited

U.S. PATENT DOCUMENTS

| | | | |
|---|---|---|---|
| 2,914,528 A | 11/1959 | Craig | |
| 2,944,053 A | 7/1960 | Edgerton | |
| 2,969,358 A | 1/1961 | Cusic | |
| 3,227,708 A | 1/1966 | Yale et al. | |
| 3,956,493 A | 5/1976 | Yale | |
| 3,966,930 A | 6/1976 | Buus et al. | |
| 3,978,216 A | 8/1976 | Fuxe | |
| 4,153,694 A | 5/1979 | Buus et al. | |
| 4,629,691 A | 12/1986 | Collins et al. | |
| 4,818,936 A | 4/1989 | Kemlo | |
| 5,051,448 A | 9/1991 | Shashoua | |
| 5,145,684 A | 9/1992 | Liversidge et al. | |
| 5,525,727 A | 6/1996 | Bodor | |
| 5,828,405 A | 10/1998 | Vanier et al. | |
| 5,966,673 A | 10/1999 | Shannon | |
| 5,983,238 A | 11/1999 | Becker et al. | |
| 5,994,392 A | 11/1999 | Shashoua et al. | |
| 6,020,954 A | 2/2000 | Aggarwal | |
| 6,121,325 A | 9/2000 | Chen et al. | |
| 6,197,764 B1 | 3/2001 | Bradley et al. | |
| 6,239,867 B1 | 5/2001 | Aggarwal | |
| 6,304,853 B1 | 10/2001 | Malnekoff | |
| 6,381,510 B1 | 4/2002 | Amidhozour et al. | |
| 6,569,853 B1 | 5/2003 | Borisy et al. | |
| 7,544,681 B2 | 6/2009 | Nudelman et al. | |
| 7,598,239 B2 | 10/2009 | Nudelman et al. | |
| 7,619,006 B2 | 11/2009 | Nudelman et al. | |
| 7,939,525 B2 | 5/2011 | Nudelman et al. | |
| 2001/0024532 A1 | 9/2001 | Malnekoff | |
| 2002/0010208 A1 | 1/2002 | Shashoua et al. | |
| 2002/0021439 A1 | 2/2002 | Priestley et al. | |
| 2002/0052170 A1 | 5/2002 | Holloway | |
| 2003/0065586 A1 | 4/2003 | Shaftel et al. | |
| 2003/0115079 A1 | 6/2003 | Rapaport | |
| 2004/0068417 A1 | 4/2004 | Sevdermish | |
| 2004/0092504 A1* | 5/2004 | Benja-Athon ................. 514/217 |
| 2004/0242570 A1 | 12/2004 | Nudelman et al. | |
| 2005/0149369 A1 | 7/2005 | Sevdermish | |
| 2006/0046967 A1 | 3/2006 | Satyam | |
| 2006/0058219 A1 | 3/2006 | Miller | |
| 2006/0142181 A1 | 6/2006 | Miller | |
| 2007/0099977 A1 | 5/2007 | Nudelman et al. | |
| 2007/0197514 A1 | 8/2007 | Nudelman et al. | |
| 2007/0219181 A1 | 9/2007 | Kimura et al. | |
| 2008/0108606 A1 | 5/2008 | Nudelman et al. | |
| 2009/0215809 A1 | 8/2009 | Yao et al. | |
| 2009/0298814 A1 | 12/2009 | Nudelman et al. | |

(Continued)

FOREIGN PATENT DOCUMENTS

| CA | 2461663 | 4/2003 |
|---|---|---|
| CN | 1596141 | 3/2005 |

(Continued)

OTHER PUBLICATIONS

Response Dated Sep. 7, 2011 to Official Action of Jul. 12, 2011 From the US Patent and Trademark Office Re. U.S. Appl. No. 11/921,578.
Translation of Final Notice of the Reason for Rejection Dated Aug. 31, 2011 From the Korean Intellectual Property Office Re. Application No. 2010-7016372.
Communication Under Rule 71(3) EPC Dated Sep. 21, 2011 From the European Patent Office Re. Application No. 02772790.8.
Response Dated Oct. 3, 2011 to Office Action of Jun. 6, 2010 From the Israeli Patent Office Re.: Application No. 161083.
Advisory Action Before the Filing of an Appeal Brief Dated Oct. 25, 2011 From the US Patent and Trademark Office Re. U.S. Appl. No. 12/764,124.

(Continued)

*Primary Examiner* — Shengjun Wang
*Assistant Examiner* — Sarah Pihonak

(57) ABSTRACT

A novel use of conjugates of psychotropic drugs (e.g., antidepressants or anti-epileptic drugs) and organic acids such as GABA in the treatment of pain is disclosed. A novel GABA conjugate and uses thereof is also disclosed.

4 Claims, 20 Drawing Sheets
(12 of 20 Drawing Sheet(s) Filed in Color)

U.S. PATENT DOCUMENTS

| | | | |
|---|---|---|---|
| 2009/0304584 | A1 | 12/2009 | Nudelman et al. |
| 2010/0063034 | A1 | 3/2010 | Nudelman et al. |
| 2010/0120755 | A1 | 5/2010 | Nudelman et al. |
| 2010/0204469 | A1 | 8/2010 | Nudelman et al. |

FOREIGN PATENT DOCUMENTS

| | | |
|---|---|---|
| EP | 0361485 | 4/1990 |
| ES | 8707175 | 10/1987 |
| GB | 829246 | 3/1960 |
| GB | 1460713 | 5/1978 |
| GB | 1514312 | 6/1978 |
| GB | 2159636 | 12/1985 |
| GB | 2358541 | 7/2001 |
| JP | 50-025574 | 3/1975 |
| JP | 53-050185 | 5/1978 |
| JP | 62-501991 | 8/1987 |
| JP | 02-128564 | 5/1990 |
| JP | 02128564 | 5/1990 |
| JP | 02-188527 | 7/1990 |
| JP | 03-017076 | 2/1991 |
| JP | 03017076 | 2/1991 |
| JP | 60-072868 | 3/1994 |
| JP | 2000-020681 | 1/2000 |
| JP | 2000020681 | 1/2000 |
| JP | 2001-201454 | 7/2001 |
| JP | 2001201454 | 7/2001 |
| WO | WO 86/04991 | 8/1986 |
| WO | WO 93/12496 | 6/1993 |
| WO | WO 97/44063 | 11/1997 |
| WO | WO 98/52898 | 11/1998 |
| WO | WO 99/26661 | 6/1999 |
| WO | WO 01/91011 | 11/2001 |
| WO | WO 02/28881 | 4/2002 |
| WO | WO 02/43652 | 6/2002 |
| WO | WO 03/026563 | 4/2003 |
| WO | WO 03/061656 | 7/2003 |
| WO | WO 03/062942 | 7/2003 |
| WO | WO 2005/032474 | 4/2005 |
| WO | WO 2005/092392 | 10/2005 |
| WO | WO 2006/027711 | 3/2006 |
| WO | WO 2006/058219 | 6/2006 |
| WO | WO 2006/131923 | 12/2006 |
| WO | WO 2007/050318 | 5/2007 |
| WO | WO 2007/139818 | 12/2007 |
| WO | WO 2008/010222 | 1/2008 |
| WO | WO 2008/010223 | 1/2008 |
| WO | WO 2009/101616 | 8/2009 |
| WO | WO 2011/104637 | 9/2011 |

OTHER PUBLICATIONS

Examiner's Report Dated Oct. 7, 2011 From the Australian Government, IP Australia Re. Application No. 2007274583.
Translation of Notice of Reason for Rejection Dated Sep. 30, 2011 From the Japanese Patent Office Re. Application No. 2007-504560.
Response Dated Oct. 3, 2011 to Examination Report of Jun. 8, 2011 From the Instituto Mexicano de la Propriedad Industrial Re. Application No. MX/a/2007/015511.
Communication Pursuant to Article 94(3) EPC Dated Apr. 11, 2011 From the European Patent Office Re. Application No. 09711260.1.
Response Dated Mar. 22, 2011 to Final Notice of the Reason for Rejection of Nov. 24, 2010 From the Korean Intellectual Property Office Re.: Application No. 2009-7024590.
Response Dated Mar. 24, 2011 to Communication Pursuant to Article 94(3) EPC of Nov. 24, 2010 From the European Patent Office Re. Application No. 07789958.1.
International Search Report and the Written Opinion Dated Mar. 30, 2011 From the International Searching Authority Re. Application No. PCT/IL2010/01041.
Office Action Dated Mar. 2, 2011 From the Israel Patent Office Re. Application No. 196538 and Its Translation Into English.
Translation of Notice of the Reason for Rejection Dated Mar. 26, 2010 From the Korean Intellectual Property Office Re.: Application No. 2004-7004581.
International Preliminary Report on Patentability Dated Aug. 26, 2010 From the International Bureau of WIPO Re. Re. Application No. PCT/IL2009/000158.
Office Action of Jul. 27, 2010 From the Israel Patent Office Re.: Application No. 199877 and Its Translation Into English.
Examiner's Report Dated Oct. 21, 2010 From the Australian Government, IP Australia Re. Application No. 2006256369.
Official Action Dated Jun. 17, 2010 From the US Patent and Trademark Office Re.: U.S. Appl. No. 12/585,021.
Response Dated Oct. 5, 2010 to Official Action of Jun. 17, 2010 From the US Patent and Trademark Office Re.: U.S. Appl. No. 12/585,021.
Examiner's Report Dated May 23, 2007 From the Government of India Patent Office Re.: Application No. 642/CHENP/2004-SPS.
Examiner's Report Dated May 2, 2007 From the Australian Government, IP Australia Re.: Application No. 2004201240.
Examiner's Report Dated Feb. 24, 2010 From the Australian Government, IP Australia Re.: Application No. 2008243147.
International Preliminary Report on Patentability Dated Oct. 12, 2006 From the International Bureau of WIPO Re.: Application No. PCT/IL2005/000341.
International Search Report Dated Jul. 11, 2003 From the International Searching Authority Re.: Application No. PCT/IL02/00795.
Invitation to Pay Additional Fees Dated Nov. 27, 2007 From the International Searching Authority Re.: Application No. PCT/IL2007/000903.
Notice of Allowance Dated Mar. 11, 2008 From the US Patent and Trademark Office Re.: U.S. Appl. No. 10/808,541.
Notice of the Reason for Rejection Dated Mar. 26, 2010 From the Korean Intellectual Property Office Re.: Application No. 2004-7004581. Korean Only.
Office Action Dated Apr. 25, 2010 From the Israel Patent Office Re.: Application No. 187892 and Its Translation Into English.
Degrand et al. "Synthesis of Nitroxides for Use as Procationic Labels and Their Incorporation Into Nafion Films", The Journal of Organic Chemistry, 58(9): 2573-2577, 1993.
Köpf-Maier et al. "An Organoid Culture Assay (OCA) for Determining the Drug Sensitivity of human Tumors", Int. J. Cancer, 51: 99-107, 1992.
Sakamoto et al. "Studies on Prodrugs. VI. Preparation and Characterization of 95-Substituted 2-Oxo-1,3-Dioxo1-4-y1)Methyl Esters of Mecillinam", Chemical and Pharmaceutical Bulletin, 35(2): 642-646, 1987. Abstract.
Vezin et al. "Biological Active Poly(N-Metacryloyl-ω-Amino Acid) Esters of Fluphenazine and Their Duration of Activity", Journal of Pharmacy and Pharmacology, British Pharmacology Conference 1979, 31(Suppl.): 63P, 1979.
Wolffe "Transcriptional Control. Sinful Repression", Nature, 387: 16017, 1997.
Luo "Pharmacokinetic Studies of Fluphenazine and Four Ester Prodrugs", A Thesis Submitted to the College of Graduate Studies and Research in Partial Fulfillment of the Requirements for the Degree of Doctor of Philosophy in the College of Pharmacy and Nutrition, University Saskatchewan, Saskatoon, Saskatchewan, Canada, p. 1-171, 1999.
Examination Report Dated Jun. 16, 2011 From the Instituto Mexicano de la Propriedad Industrial Re. Application No. PA/a/2006/010924.
Office Action Dated Jun. 6, 2010 From the Israeli Patent Office Re.: Application No. 161083 and Its Translation Into English.
Response Dated Jun. 23, 2010 to Notice of the Reason for Rejection of Feb. 24, 2010 From the Korean Intellectual Property Office Re.: Application No. 2009-7024590.
Response Dated Jun. 23, 2010 to Notice of the Reason for Rejection of Mar. 26, 2010 From the Korean Intellectual Property Office Re.: Application No. 2004-7004581.
Official Action Dated Mar. 14, 2011 From the US Patent and Trademark Office Re. U.S. Appl. No. 12/764,124.
Response Dated Jul. 6, 2011 to Official Action of Mar. 14, 2011 From the US Patent and Trademark Office Re. U.S. Appl. No. 12/764,124.
Translation of Office Action Dated Jul. 12, 2010 From the State Intellectual Property Office of the People's Republic of China Re. Application No. 200780033294.6.
Office Action Dated Mar. 2, 2011 From the Israeli Patent Office Re. Application No. 196538.
Response Dated Aug. 2, 2011 to Office Action of Mar. 2, 2011 From the Israeli Patent Office Re. Application No. 196538.

Response Dated Jul. 24, 2011 to Communication Pursuant to Article 94(3) EPC of Apr. 11, 2011 From the European Patent Office Re. Application No. 09711260.1.
Response Dated Jul. 26, 2011 to Official Action of Mar. 14, 2011 From the US Patent and Trademark Office Re. U.S. Appl. No. 12/764,124.
Response Dated Jul. 26, to Communication Pursuant to Rules 70(2) and 70a(2) EPC of Jan. 31, 2011 From the European Patent Office Re. Application No. 10182948.9.
Official Action Dated Aug. 5, 2011 From the US Patent and Trademark Office Re. U.S. Appl. No. 12/764,124.
Translation of Notice of Final Rejection Dated May 30, 2011 From the Korean Intellectual Property Office Re. Application No. 2010-7016372.
Translation of Notice of Final Rejection Dated May 30, 2011 From the Korean Intellectual Property Office Re.: Application No. 2009-7024590.
Interview Summary Dated Jan. 27, 2011 From the US Patent and Trademark Office Re.: U.S. Appl. No. 12/585,021.
Notice of Allowance Dated Mar. 21, 2011 From the US Patent and Trademark Office Re.: U.S. Appl. No. 12/585,021.
Official Action Dated Jul. 12, 2011 From the US Patent and Trademark Office Re. U.S. Appl. No. 11/921,578.
Response Dated Mar. 9, 2011 to Official Action of Dec. 14, 2010 From the US Patent and Trademark Office Re.: U.S. Appl. No. 12/585,021.
Response Dated Jun. 16, 2011 to Communication Pursuant to Article 94(3) EPC of Dec. 16, 2010 From the European Patent Office Re. Application No. 02772790.8.
Interview Summary Dated May 6, 2011 From the US Patent and Trademark Office Re. U.S. Appl. No. 12/656,048.
Official Action Dated Aug. 25, 2011 From the US Patent and Trademark Office Re. U.S. Appl. No. 12/655,048.
Requisition by the Examiner Dated Aug. 2, 2011 From the Canadian Intellectual Property Office Re. Application No. 2,560,905.
Translation of Notice of Reason for Rejection Dated Nov. 2, 2010 From the Japanese Patent Office Re. Application No. 2007-504560.
Translation of Notice of the Reason for Rejection Dated Oct. 28, 2010 From the Korean Itellectual property Office Re. Application No. 2010-7016372.
Communication Pursuant to Article 96(2) EPC Dated Nov. 24, 2006 From the European Patent Office Re.: Application No. 02772790.8.
Communication Relating to the Results of the Partial International Search Dated Nov. 27, 2007 From the International Searching Authority Re.: Application No. PCT/IL2007/000903.
International Preliminary Report on Patentability Dated Jan. 29, 2009 From the International Bureau of WIPO Re.: Application No. PCT/IL2007/000902.
International Preliminary Report on Patentability Dated Jan. 29, 2009 From the International Bureau of WIPO Re.: Application No. PCT/IL2007/000903.
Official Action Dated Jun. 19, 2008 From the US Patent and Trademark Office Re.: U.S. Appl. No. 11/636,599.
Official Action Dated Oct. 31, 2008 From the US Patent and Trademark Office Re.: U.S. Appl. No. 12/005,342.
Communication Relating to the Results of the Partial International Search Dated Jun. 13, 2006 From the International Searching Authority Re.: Application No. PCT/IL2005/000341.
Communication Relating to the Results of the Partial International Search Dated Nov. 20, 2007 From the International Searching Authority Re.: Application No. PCT/IL2007/000902.
Communication Under Rule 112 EPC Dated Oct. 2, 2007 From the European Patent Office Re.: Application No. 05718914.4.
International Search Report Dated Feb. 12, 2008 From the International Searching Authority Re.: Application No. PCT/IL2007/000903.
International Search Report Dated Feb. 13, 2008 From the International Searching Authority Re.: Application No. PCT/IL2007/000902.
International Search Report Dated Aug. 23, 2006 From the International Searching Authority Re.: Application No. PCT/IL2005/000341.
International Search Report Dated Jun. 25, 2009 From the International Searching Authority Re.: Application No. PCT/IL2009/000158.
Invitation to Pay Additional Fees Dated Jun. 13, 2006 From the International Searching Authority Re.: Application No. PCT/IL2005/000341.
Invitation to Pay Additional Fees Dated Nov. 20, 2007 From the International Searching Authority Re.: Application No. PCT/IL2007/000902.
Notice of Allowance Dated Jul. 10, 2009 From the US Patent and Trademark Office Re.: U.S. Appl. No. 11/636,599.
Office Action Dated Aug. 8, 2008 From the Patent Office of the People's Republic of China Re.: Application No. 02823600.9.
Office Action Dated Sep. 9, 2005 From the Patent Office of the People's Republic of China Re.: Application No. 02823600.9 and Its Translation Into English.
Office Action Dated Feb. 14, 2008 From the Government of India Patent Office Re.: Application No. 642/CHENP/2004-SPS.
Office Action Dated May 15, 2008 From the Government of India Patent Office Re.: Application No. 642/CHENP/2004-SPS.
Office Action Dated Feb. 27, 2009 From the Israeli Patent Office Re.: Application No. 161083 and Its Translation Into English.
Official Action Dated Feb. 1, 2007 From the US Patent and Trademark Office Re.: U.S. Appl. No. 10/808,541.
Official Action Dated May 9, 2008 From the US Patent and Trademark Office Re.: U.S. Appl. No. 11/636,599.
Official Action Dated May 16, 2008 From the US Patent and Trademark Office Re.: U.S. Appl. No. 11/636,594.
Official Action Dated Sep. 16, 2008 From the US Patent and Trademark Office Re.: U.S. Appl. No. 12/005,342.
Official Action Dated Apr. 17, 2008 From the US Patent and Trademark Office Re.: U.S. Appl. No. 11/636,594.
Official Action Dated Feb. 17, 2009 From the US Patent and Trademark Office Re.: U.S. Appl. No. 11/636,599.
Official Action Dated Jul. 25, 2006 From the US Patent and Trademark Office Re.: U.S. Appl. No. 10/808,541.
Official Action Dated Mar. 30, 2006 From the US Patent and Trademark Office Re.: U.S. Appl. No. 10/808,541.
Response Dated Nov. 23, 2009 to Office Action of Jul. 23, 2009 From the Israel Patent Office Re.: Application No. 199877.
Supplementary European Search Report Dated Apr. 25, 2006 From the European Patent Office Re.: Application No. 02772790.8.
Translation of Notice for Reason for Rejection Dated Oct. 20, 2009 From the Japanese Patent Office Re.: Application No. 2003-530202.
Translation of Notice of Reason for Rejection Dated Feb. 10, 2009 From the Japanese Patent Office Re.: Application No. 2003-530202.
Translation of Notice of the Reason for Rejection Dated Aug. 26, 2009 From the Korean Intellectual Property Office Re.: Application No. 2004-7004581.
Translation of Office Action Dated Jul. 17, 2009 From the State Intellectual Property Office of the People's Republic of China Re.: Application No. 200580017025.1.
Written Opinion Dated Feb. 12, 2008 From the International Searching Authority Re.: Application No. PCT/IL2007/000903.
Written Opinion Dated Feb. 13, 2008 From the International Searching Authority Re.: Application No. PCT/IL2007/000902.
Written Opinion Dated Aug. 23, 2006 From the International Searching Authority Re.: Application No. PCT/IL2005/000341.
Written Opinion Dated Jun. 25, 2009 From the International Searching Authority Re.: Application No. PCT/IL2009/000158.
Budavari et al. "The Merck Index", Merck & Co., USA, 12th Ed., 1996. P.Ther-8, First Col., 6th Line From the Bottom, 2nd Col., Line 13.
Budavari et al. "The Merck Index", Merck & Co., USA, 12th Ed, 1996, p. 1260. p. 1260, § 1.
Budavari et al. "The Merck Index", Merck & Co., USA, 12th Ed., 1996, p. 1246. p. 1246, Last §.
Capasso et al. "Anticonvulsive Activity of a New GABA Mimetic Drug", European Neuropsychopharmacology, 7: 57-63, 1997.
Degrand et al. "Synthesis of Nitroxides for Use as Procationic Labels and Their Incorporation Into Nation Films", The Journal of Organic Chemistry, 58(9): 2573-2577, 1993.

Dutta et al. "Existing Dopaminergic Therapies for Parkinson's Disease", Expert Opinion on Therapeutic Patents, XP002531574, 16: 1613-1625, 2006. § [04.1], Fig. 1.
Fingl et al. "General Principles", The Pharmacological Basis of Therapeutics, Chap. 1: 1-46, 1975.
Florence et al. "Prolongation of the Action of Intramuscular Formulations of Phenothiazines", Optimization of Drug Delivery, 17th Alfred Benzon Symposium, Mungsgaard, Copenhagen, p. 93-111, 1982.
Geyer et al. "Animal Behavior Models of the Mechanisms Underlying Antipsychotic Atypicality", Progress in Neuro-Psychopharmacology & Biological Psychiatry, 27: 1071-1079, 2003.
Hadad et al. "Pharmacokinetic Analysis and Antiepileptic Activity of N-Valproyl Derivatives of GABA and Glycine", Pharmaceutical Research, 112(6): 905-910, 1995.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
McCaffrey et al. "A Rapid Fluorometric DNA Assay for the Measurement of Cell Density and Proliferation In Vitro", In Vitro Cellular Development Biology, 24(3): 247-252, 1988. Abstract.
Merck "Schizophrenia", the Merck Manuals, Section Psychiatric Disorders, 17th Ed.: 1569-1575, Dec. 10, 1999. Japanese Version and Its Translation Into English. p. 1572, Right Col., Line 15—p. 1573, Left Col., Line 11, p. 1574, Table 193-1.
Napolitano et al. "New Directions in Parkinson's Research and Treatment", Expert Opinion on Therapeutic Patents, XP002531575, 8: 1251-1268, 1998. Fig.4.
Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, 58: 1229-1236, 1999.
Pouzet et al. "Effects of the 5-HT7 Receptor Antagonist SB-258741 in Animal Models for Schizophrenia", Pharmacology, Biochemistry and Behavior, 71: 655-665, 2002.
Quadri et al. "Effects of Centrally Acting Drugs on Serum Prolactin Levels in Rhesus Monkeys", Neuroendocrinology, 27(3-4): 136-147, 1978. Abstract.
Rephaeli et al. "Observation of Sequence-Dependent Interaction Between Prodrugs of Carboxylic-Acid-Esters and Doxorubicin in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.
Scriba "Phenytoin-Lipid Conjugates as Potential Prodrugs of Phenytoin", Archiv der Pharmazie, VCH—Verlagsgesellschaft MBH, Weinheim, DE, 326(8): 477-481, 1993. Scheme 1, p. 147.
Scriba et al "Anticonvulsant Activity of Phenytoin-Lipid Conjugates, A New Class of Phenytoin Prodrugs"—Journal of Pharmaceutical Pharmacology, 47: 197-203, 1996. Scheme 1, p. 198, Abstract.
Scriba et al. "Synthesis and Anticovulsant Activity of N-Benzyloxycarbonyl-Amino Acid Prodrugs of Phenytoin", Journal of Pharmacy and Pharmacology, 51: 549-553, 1999.
Shalitin et al. "The Effect of Angiotensin II on Myosin Heavy Chain Expression in Cultured Myocardial Cells", In Vitro Cellular Development Biology—Animal, 32: 573-578, 1996.
Toth "A Novel Chemical Approach to Drug Delivery: Lipidic Amino Acid Conjugates", Journal of Drug Targeting, 2(3): 217-239, 1994. p. 223, Col. II, 3rd §.
Wolfe "Transcriptional Control. Sinful Repression", Nature, 387: 16017, 1997.
Worms et al. "Dopamine-Like Activities of an Aminopyridazinde Derivative, CM 30366: A Behavioural Study", Naunyn-Schmiedeberg's Archives of Pharmacology, 334: 246-252, 1986.
Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, 17: 2325-2327, 2003. Abstract.

Zaugg et al. "Modification of Hemoglobin With Analogs of Aspirin", The Journal of Biological Chemistry, 255(7): 2816-2821, 1980.
Response Dated Feb. 23, 2011 to Examiner's Report of Feb. 24, 2010 From the Australian Government, IP Australia Re.: Application No. 2008243147.
"New Edition of Pharmaceutics", People's Hygiene Publishing House, 14: 178, 1998. Abstract in Chinese Only!
Communication Pursuant to Article 94(3) Dated Apr. 2, 2008 From the European Patent Office Re.: Application No. 06756205.8.
Office Action Dated Feb. 15, 2009 From the Israeli Patent Office Re.: Application No. 161083.
Translation of Notice of the Reason for Rejection Dated Feb. 24, 2010 From the Korean Intellectual Property Office Re.: Application No. 2009-7024590.
Translation of Office Action Dated Jan. 29, 2010 From the State Intellectual Property Office of the People's Republic of China Re.: Application No. 200680029378.8.
Official Action Dated Jun. 23, 2011 From the US Patent and Trademark Office Re. U.S. Appl. No. 12/373,542.
English Summary of Examination Report Dated Sep. 4, 2007 From the Instituto Mexicano de la Propriedad Industrial Re. Application No. PA/a/2004/002912.
Examination Report Dated Sep. 20, 2010 From the Instituto Mexicano der la Propriedad Industrial Re. Application No. MX/a/2007/015511 and Its Translation Into English.
Office Action Dated Jun. 24, 2011 From the State Intellectual Property Office of the People's Republic of China Re. Application No. 200780033294.6 and Its Translation Into English.
Response Dated May 5, 2011 to Requisition by the Examiner of Nov. 8, 2010 From the Canadian Intellectual Property Office Re. Application No. 2,461,663.
Response Dated Jun. 6, 2011 to Official Action of Jan. 6, 2011 From the US Patent and Trademark Office Re. U.S. Appl. No. 12/656,048.
Response Dated Feb. 18, 2011 to Examination Report Dated Sep. 20, 2010 From the Instituto Mexicano der la Propriedad Industrial Re. Application No. MX/a/2007/015511 and Its Translation Into English.
Response Dated Aug. 22, 2011 to Office Action of Jun. 24, 2011 From the State Intellectual Property Office of the People's Republic of China Re. Application No. 200780033294.6.
Official Action Dated Aug. 25, 2010 From the US Patent and Trademark Office Re. U.S. Appl. No. 12/764,124.
Response Dated Sep. 1, 2010 to Office Action of Apr. 25, 2010 From the Israel Patent Office Re.: Application No. 187892.
Examination Report Dated Aug. 25, 2010 From the Instituto Mexicano de la Propriedad Industrial Re. Application No. PA/a/2004/002912 and Its Summary in English.
Communication Pursuant to Article 94(3) EPC Dated Dec. 16, 2010 From the European Patent Office Re. Application No. 02772790.8.
Communication Pursuant to Article 94(3) EPC Dated Nov. 24, 2010 From the European Patent Office Re. Application No. 07789958.1.
Requisition by the Examiner Dated Nov. 8, 2010 From the Canadian Intellectual Property Office Re. Application No. 2,461,663.
Response Dated Nov. 8, 2010 to Office Action of Jul. 12, 2010 From the State Intellectual Property Office of the People's Republic of China Re. Application No. 200780033294.6.
Response Dated Nov. 16, 2010 to Examination Report of Aug. 25, 2010 From the Instituto Mexicano de la Propriedad Industrial Re. Application No. PA/a/2004/002912.
Response Dated Dec. 20, 2010 to Notice of the Reason for Rejection of Oct. 28, 2010 From the Korean Itellectual property Office Re. Application No. 2010-7016372.
Translation of Final Notice of the Reason for Rejection Dated Nov. 24, 2010 From the Korean Intellectual Property Office Re.: Application No. 2009-7024590.
Ogiso et al. "Pharmacokinetic Analysis of Phenytoin and Its Derivatives in Plasma and Brain in Rats", Biological and Pharmaceutical Bulletin, XP002613683, 16(10): 1025-1030, Oct. 1, 1993.
Official Action Dated Dec. 14, 2010 From the US Patent and Trademark Office Re.: U.S. Appl. No. 12/585,021.
Response Dated Dec. 23, 2010 to Office Action of Aug. 23, 2010 From the Israel Patent Office Re. Application No. 203058.

European Search Report and the European Search Opinion Dated Dec. 30, 2010 From the European Patent Office Re. Application No. 10182948.9.

Official Action Dated Jan. 6, 2011 From the US Patent and Trademark Office Re. U.S. Appl. No. 12/656,048.

Carducci et al. "Phenylbutyrate Induces Apoptosis in Human Prostate Cancer and Is More Potent Than Phenylacetate", Clinical Cancer Research, XP002613699, 2(2): 379-387, 1996. Abstract.

Coradini et al. "Effect of Sodium Butyrate on Human Breast Cancer Cell Lines", Cell Proliferation, XP002613698, 30(3-4) Mar. 1997. Abstract.

Luo et al. "Comparative Pharmacokinetic Analysis of Fluphenazine and Four Ester Prodrugs", Pharmaceutical Research, XP008130430, 14(11 Suppl.): S360, # 2441, Nov. 1997. & Annual Meeting of the American Association of Pharmaceutical Scientists, Boston, MA, USA, Nov. 2-6, 1997.

Milovic "Effect of Structural Analogues of Propionate and Butyrate on Colon Cancer Cell Growth", International Journal of Colorectal Disease, XP002613700, 15(5-6): 264-270, 2000. Abstract, p. 267, Table 2.

Velázquez et al. "Butyrate Inhibits Seeding and Growth of Colorectal Metastases to the Liver in Mice", Surgery, XP005473855, 120(2): 440-448, Aug. 1, 1996. Abstract.

Examination Report Dated Jun. 8, 2011 From the Instituto Mexicano de la Propriedad Industrial Re. Application No. MX/a/2007/015511 and Its Summary Into English.

Response Dated Feb. 25, 2011 to Official Action of Aug. 25, 2010 From the US Patent and Trademark Office Re. U.S. Appl. No. 12/764,124.

Office Action Dated Aug. 23, 2010 From the Israel Patent Office Re. Application No. 203058 and Its Translation Into English.

Response Dated Sep. 18, 2011 to Examination Report of Jun. 16, 2011 From the Instituto Mexicano de la Propriedad Industrial Re. Application No. PA/a/2006/010924.

International Preliminary Report on Patentability Dated Oct. 17, 2007 From the International Preliminary Examining Authority Re.: Application No. PCT/IL2006/000666.

Communication Relating to the Results of the Partial International Search Dated May 10, 2007 From the International Searching Authority Re.: Application No. PCT/IL2006/000666.

International Preliminary Report on Patentability Dated Dec. 3, 2007 From the International Preliminary Examining Authority Re.: Application No. PCT/IL2006/000666.

International Search Report and the Written Opinion Dated Dec. 3, 2007 From the International Searching Authority Re.: Application No. PCT/IL2006/000666.

Official Action Dated Feb. 16, 2010 From the US Patent and Trademark Office Re.: U.S. Appl. No. 12/585,021.

Response Dated Mar. 3, 2010 to Official Action of Feb. 16, 2010 From the US Patent and Trademark Office Re.: U.S. Appl. No. 12/585,021.

Response Dated Jan. 13, 2010 to Notice for Reason for Rejection of Oct. 20, 2009 From the Japanese Patent Office Re.: Application No. 2003-530202.

Response Dated Jan. 13, 2010 to Office Action of Jul. 17, 2009 From the State Intellectual Property Office of the People's Republic of China Re.: Application No. 200580017025.1.

Response Dated Dec. 30, 2009 to Office Action of Aug. 31, 2009 From the Israel Patent Office Re.: Application No. 161083.

BioLineRx "BioLineRx Announces Positive Topline Results for BL-1020, A First in Class GABA Enhanced Antipsychotic for the Treatment of Schizophrenia. BL-1020 Meets Primary and Secondary Efficacy Endpoints From the Pahase 2b EAGLE Trial", BioLine Rx, 4 P., Sep. 14, 2009.

Chan et al. "Phenothiazine Inhibitors of Trypanothione Reductase as Potential Antitrypanosomal and Antileishmanial Drugs", Journal of medicinal Chmeistry, 41(2): 148-156, 1998.

Gil-Ad et al. "Novel Anti-Psychotics That Display GABAergic Acitivity and Decreased Extrapyramidal Side Effects, for the Treatment of Schizophrenia and Related Psychiatric Disorders", Neural Plasticity, 10(3): 200, 2003. Abstract.

Ware et al. "An Automated Approach to Salt Selection for New Unique Trazodone Salts", Pharmaceutical Research, 21(1): 177-184, 2004. Abstract.

Wilson et al. "Central Nervous System Depressant", Wilson and Gisvold's Textbook of Organic Medicinal and Pharmaceutical Chemistry, 8th Ed., p. 362-371, 1982.

Response Dated Feb. 9, 2011 to Office Action of Aug. 11, 2010 From the State Intellectual Property Office of the People's Republic of China Re. Application No. 200810190781.X.

Response Dated Nov. 28, 2010 to Office Action of Jul. 27, 2010 From the Israel Patent Office Re.: Application No. 199877.

Translation of Office Action Dated Aug. 11, 2010 From the State Intellectual Property Office of the People's Republic of China Re. Application No. 200810190781.X.

Examination Report Dated May 30, 2011 From the Instituto Mexicano de la Propriedad Industrial Re. Application No. PA/a/2004/002912 and Its Summary in English.

Notice of Allowance Dated May 29, 2009 From the US Patent and Trademark Office Re.: U.S. Appl. No. 12/005,342.

Office Action Dated May 17, 2011 From the Israel Patent Office Re.: Application No. 187892 and Its Translation Into English.

Response Dated May 1, 2006 to Official Action of Mar. 30, 2006 From the US Patent and Trademark Office Re.: U.S. Appl. No. 10/808,541.

Response Dated Dec. 3, 2007 to Official Action of Feb. 1, 2007 From the US Patent and Trademark Office Re.: U.S. Appl. No. 10/808,541.

Response Dated Oct. 13, 2008 to Official Action of Sep. 16, 2008 From the US Patent and Trademark Office Re.: U.S. Appl. No. 12/005,342.

Response Dated Nov. 15, 2006 to Official Action of Jul. 25, 2006 From the US Patent and Trademark Office Re.: U.S. Appl. No. 10/808,541.

Response Dated Feb. 24, 2009 to Official Action of Oct. 31, 2008 From the US Patent and Trademark Office Re.: U.S. Appl. No. 12/005,342.

Supplemental Response Dated Mar. 31, 2009 to Response of Feb. 24, 2009 From the US Patent and Trademark Office Re.: U.S. Appl. No. 12/005,342.

Response Dated Jun. 6, 2010 to Office Action of Jan. 29, 2010 From the State Intellectual Property Office of the People's Republic of China Re.: Application No. 200680029378.8.

Communication Pursuant to Rules 70(2) and 70a(2) EPC Dated Jan. 31, 2011 From the European Patent Office Re. Application No. 10182948.9.

Response Dated Jan. 18, 2011 to Notice of Reason for Rejection of Nov. 2, 2010 From the Japanese Patent Office Re. Application No. 2007-504560.

Official Action Dated Oct. 21, 2011 From the US Patent and Trademark Office Re. U.S. Appl. No. 12/373,542.

Response Dated Oct. 19, 2011 to Official Action Dated Aug. 5, 2011 From the US Patent and Trademark Office Re. U.S. Appl. No. 12/764,124.

Response Dated Oct. 23, 2011 to Office Action Dated May 17, 2011 From the Israel Patent Office Re.: Application No. 187892.

Bousquct et al. "Synthesis, Physical Properties, Toxicological Studies and Bioavailability of L-Pyroglutamic and L-Glutamic Acid Esters of Paracetamol as Potentially Prodrugs", Journal of Pharmacy and Pharmacology, 48: 479-485, Jan. 1996.

Office Action Dated Dec. 12, 2011 From the Israel Patent Office Re.: Application No. 187892 and Its Translation Into English.

Official Action Dated Nov. 1, 2011 From the US Patent and Trademark Office Re. U.S. Appl. No. 11/921,578.

Bastin et al. "Salt Selection and Optimisation Procedures for Pharmaceutical New Chemical Entities", Organic Process Research & Development, 4: 427-435, 2000.

Response Dated Nov. 24, 2011 to Official Action of Aug. 25, 2011 From the US Patent and Trademark Office Re. U.S. Appl. No. 12/655,048.

Supplemental After Final Amendment Dated Nov. 17, 2011 in Response to Official Action Dated Aug. 5, 2011 From the US Patent and Trademark Office Re. U.S. Appl. No. 12/764,124.

Translation of Office Action Dated Nov. 3, 2011 From the State Intellectual Property Office of the People's Republic of China Re.: Application No. 200580017025.1.
Requisition by the Examiner Dated Aug. 2, 2011 From the Canadian Intellectual Property Office Re. Application No. 2,461,663.
International Search Report and the Written Opinion Dated Dec. 1, 2011 From the International Searching Authority Re. Application No. PCT/IB2011/000915.
Notice of Allowance Dated Dec. 1, 2011 From the US Patent and Trademark Office Re. U.S. Appl. No. 12/764,124.
Advisory Action Before the Filing of an Appeal Brief Dated Jan. 10, 2012 From the US Patent and Trademark Office Re. U.S. Appl. No. 12/655,048.
Examination Report Dated Dec. 5, 2011 From the Instituto Mexicano de la Propriedad Industrial Re. Application No. MX/a/2009/000641 and Its Summary in English.
Examiner's Report Dated Jan. 24, 2012 From the Australian Government, IP Australia Re. Application No. 2006256369.
Communication Pursuant to Article 94(3) EPC Dated Jan. 26, 2012 From the European Patent Office Re. Application No. 10182948.9.
Communication Under Rule 71(3) EPC Dated Feb. 20, 2012 From the European Patent Office Re. Application No. 09711260.1.
Examination Report Dated Jan. 19, 2012 From the Instituto Mexican de la Propriedad Industrial Re. Application No. MX/a/2007/015511 and Its Translation Into English.
International Search Report and the Written Opinion Dated Feb. 8, 2012 From the International Searching Authority Re.: Application No. PCT/IL2011/000752.
Notice of Allowance Dated Feb. 23, 2012 From the US Patent and Trademark Office Re. U.S. Appl. No. 12/867,055.
Official Action Dated Feb. 2, 2012 From the US Patent and Trademark Office Re. U.S. Appl. No. 12/655,048.
Official Action Dated Jan. 31, 2012 From the US Patent and Trademark Office Re. U.S. Appl. No. 13/034,453.
Summons to Attend Oral Proceedings Pursuant to Rule 115(1) EPC Dated Jan. 26, 2012 From the European Patent Office Re. Application No. 06756205.8.
Translation of Office Action Dated Jan. 5, 2012 From the State Intellectual Property Office of the People's Republic of China Re. Application No. 200810190781.X.
Translation of Office Action Dated Feb. 23, 2012 From the State Intellectual Property Office of the People's Republic of China Re. Application No. 200780033294.6.
Translation of Office Action Dated Jan. 30, 2012 From the State Intellectual Property Office of the People's Republic of China Re.: Application No. 200680029378.8.
Morissette et al. "High-Througput Crystallization: Polymorphs, Salts, Co-Crystals and Solvates of Pharmaceutical Solids", Advanced Drug Delivery Reviews, 56: 275-300, 2004.
Rephaeli et al. "Gamm-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.

* cited by examiner

* Nortriptyline vs nortriptylineGABA p<0.05
Nortriptyline vs control p<0.05
+ NortriptylineGABA vs control p<0.05

—♦—Control

—■—Nortriptyline 0.2 mg/kg

- × - Nortriptyline-GABA eq 0.2 mg/kg

* Nortriptyline vs nortriptyline-GABA p<0.05
Nortriptyline vs control p<0.05
+ NortriptylineGABA vs control p<0.05

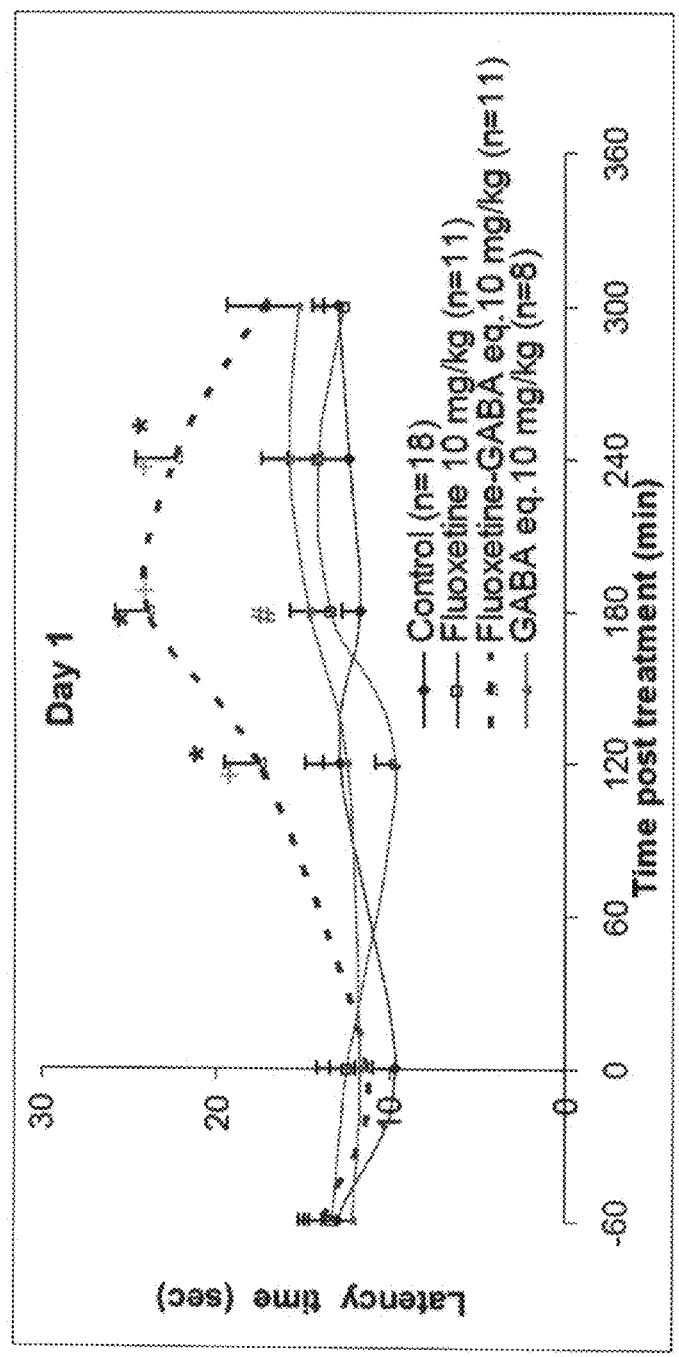

— Control
— Fluoxetine 10 mg/kg
- △ - Fluoxetine-GABA eq.10 mg/kg

\* Fluoxetine vs Fluoxetine GABA $p<0.05$
\# Fluoxetine vs control $p<0.05$
✢ Fluoxetine GABA vs control $p<0.05$ significant vs. control * vs. Nortriptyline

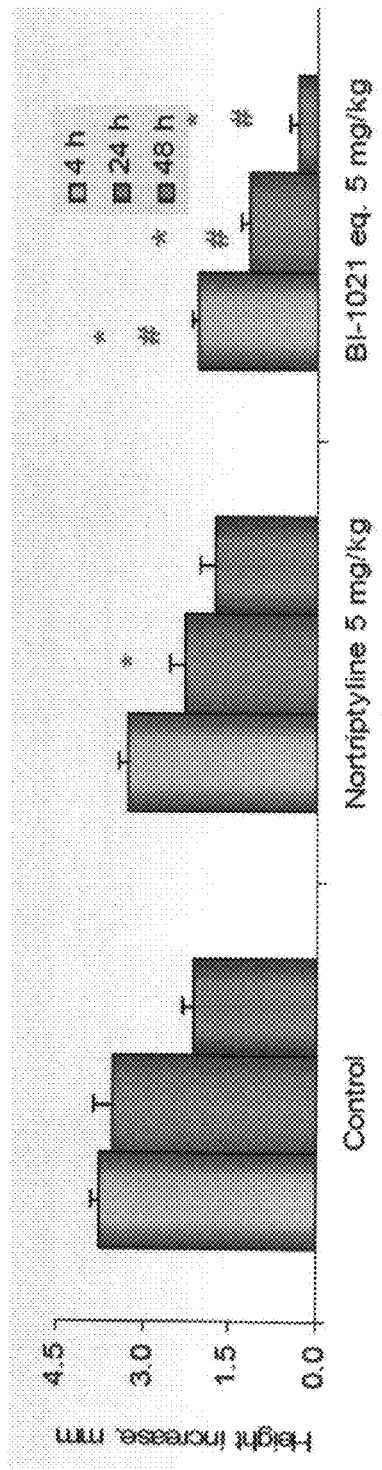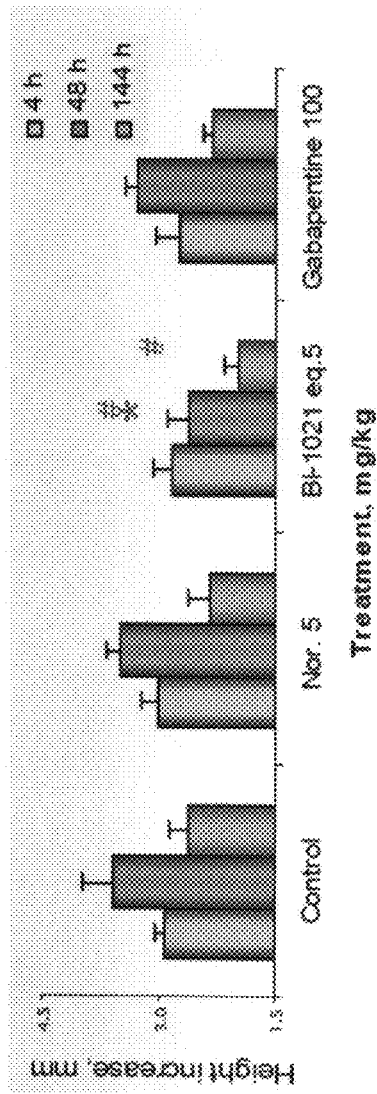
Fig. 13a
Fig. 13b

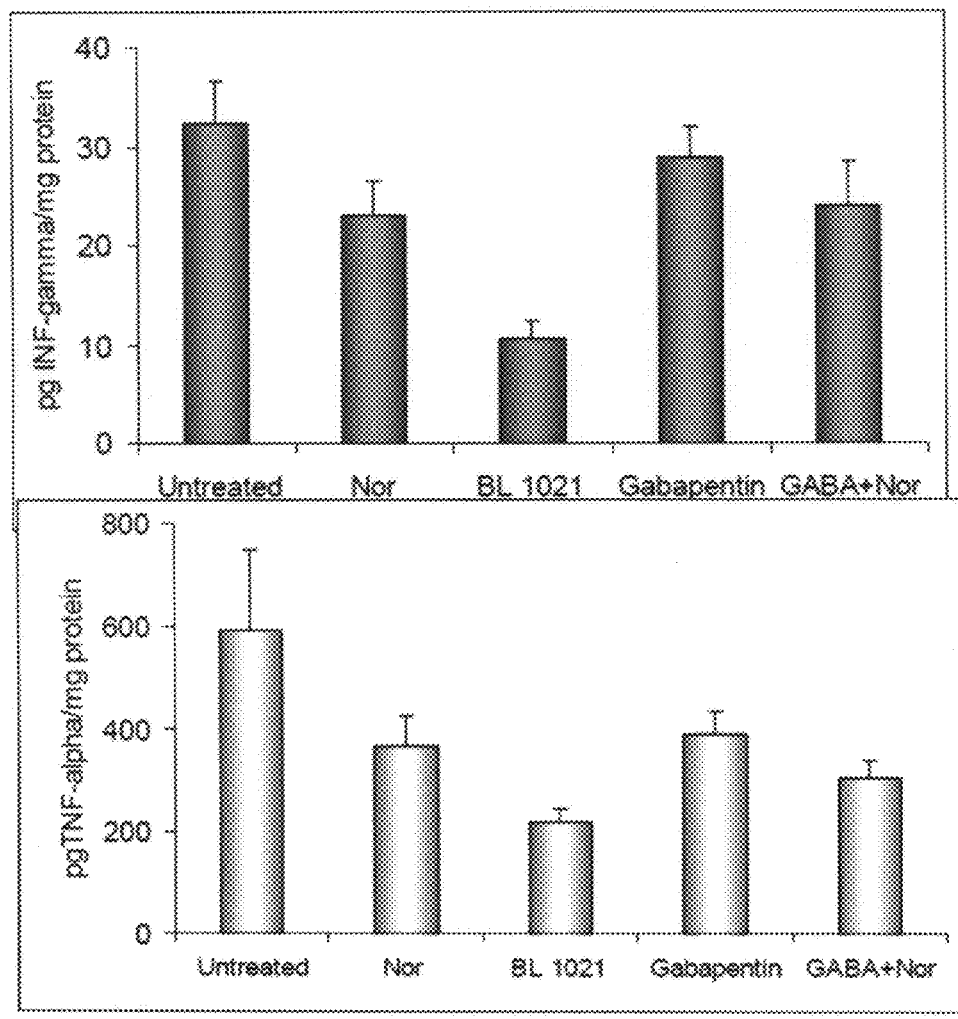

CONJUGATES COMPRISING A PSYCHOTROPIC DRUG OR A GABA AGONIST AND AN ORGANIC ACID AND THEIR USE IN TREATING PAIN AND OTHER CNS DISORDERS

RELATED APPLICATIONS

This Application is a National Phase of PCT Patent Application No. PCT/IL2007/000903 having International filing date of Jul. 17, 2007, which claims the benefit of U.S. Provisional Patent Application Nos. 60/831,192 filed on Jul. 17, 2006 and 60/831,195 filed on Jul. 17, 2006. The contents of the above Applications are all incorporated herein by reference.

FIELD AND BACKGROUND OF THE INVENTION

The present invention relates to the field of pharmacology and, more particularly, to the treatment of pain.

Inadequate pain management is widely prevalent and harmful to patients. Numerous studies have demonstrated poor control of post-operative and trauma pain, cancer pain and chronic non-cancer pain. Thus, there is a continuing need for medications able to provide high efficacy pain relief while reducing the possibility of undesirable effects.

Pain can be classified into two main categories, acute and chronic, differing in their etiology, pathophysiology, diagnosis and treatment. Acute pain is nociceptive in nature (i.e. resulting directly from local tissue injury). It is a normal, predictable physiological response to an adverse chemical, thermal, or mechanical stimulus associated with surgery, trauma, or acute illness. It is normally self-limited such that when the condition producing the pain resolves, the pain disappears. Chronic pain may be defined as pain persisting longer than the expected time of tissue healing. Injury or a disease process can trigger chronic pain, but other factors besides the triggering event can perpetuate the pain. Chronic pain may be either neuropathic (i.e. initiated or caused by a primary lesion or dysfunction in the nervous system) or nociceptive.

Nociceptive pain is typically treated with anti-inflammatory or analgesic medications whereas neuropathic pain is usually treated with medications that influence neurotransmitters. These include, for example, antidepressants, and antiepileptic drugs. Patients with refractory neuropathic pain are typically treated with opioids.

One neurotransmitter which is known to be involved in the complex circuitry underlying pain is the inhibitory neurotransmitter, gamma-amino butyric acid (GABA). GABA is not transported efficiently into the brain from the bloodstream because of poor transport properties that prevent passage through the blood-brain barrier. Consequently, brain cells synthesize virtually all of the GABA found in the brain (by decarboxylation of glutamic acid with pyridoxal phosphate).

GABA regulates neuronal excitability through binding to specific membrane proteins (i.e., GABA receptors), which results in opening of an ion channel. The entry of chloride ion through the ion channel leads to hyperpolarization of the recipient cell, which consequently prevents transmission of nerve impulses to other cells.

Although most commonly used for the treatment of anxiety, muscle spasms and epilepsy, GABA agonists have been shown to alleviate the symptoms of pain through a number of mechanisms. For example, pain may be reduced by potentiating GABA transmission. This may involve targeting GABA transporters as well as GABA associated enzymes and receptors, such as the GABA-B receptors [Frediani F. Neurol Sci. 2004, Suppl 3:S161-6]. In addition, GABA agonists may alleviate pain by reducing glutamate-mediated excitatory transmission and/or blocking voltage-activated ion channels. The latter mechanism of action is exemplified by the newer generation of antiepileptics such as lamotrigine and gabapentin in the clinical treatment of neuropathic pain symptoms [Blackburn-Munro G., et al., Curr Pharm Des. 2005; 11 (23): 2961-76].

The use of GABA agonists is limited since they typically include hydrophilic functional groups (e.g., a free carboxylic acid group and a free amino group) and therefore do not readily cross the blood brain barrier (BBB). As such, invasive methods of delivery are required for GABA agonists to have a therapeutic effect. However, it was found that chemical conjugation of such compounds with fatty amino acids or peptides could facilitate to some extent their passage across the BBB [Toth I. J. Drug Target 1994, 2, 217-39].

Despite considerable progress in developing new compounds, the use of systemically acting GABA agonists (e.g., gabapentin, pregabalin and various benzodiazepines) is limited by adverse side-effects such as sedation and nausea.

The neurotransmitters norepinephrine and serotonin are functionally inhibitory on pain transmission. Thus, as mentioned hereinabove, monoamine up-regulators such as antidepressants and antiepileptics are also used in the clinical management of pain.

Tricyclic antidepressants are thought to affect pain transmission in the spinal cord by inhibiting the reuptake of norepinephrine and serotonin, both of which influence descending pain pathways. In addition, histamine H1-receptor affinity (associated with sedation) may be correlated with the analgesic effect of antidepressants.

Tricyclic antidepressants may be categorized as secondary or tertiary amines. Secondary amines such as nortriptyline (Pamelor) and desipramine (Norpramin) show relatively selective inhibition of norepinephrine reuptake. Tertiary amines such as amitriptyline and imipramine (Tofranil) exhibit a more balanced inhibition of norepinephrine and serotonin, however, they also have greater anticholinergic side effects. The novel antidepressants venlafaxine (Effexor) and duloxetine (Cymbalta) comprise a balanced inhibition of serotonin and norepinephrine reuptake without blockade of other neuroreceptors that are responsible for typical tricyclic side effects. The mechanism of action of bupropion (Wellbutrin) is uncertain but involves blockade of dopamine uptake.

The efficacy of antidepressant drugs varies dramatically for neuropathic and non-neuropathic pain syndromes. In addition, specific agents within each medication class can vary in effectiveness.

For example, antidepressants with mixed-receptor or noradrenergic activity appear to have the greatest therapeutic effect in patients with neuropathic pain. Predominantly serotoninergic drugs, such as selective serotonin reuptake inhibitors (SSRIs), are ineffective in treating chronic pain [McQuay H J, et al., Pain 1996; 68:217-27]. Amitriptyline and its metabolite nortriptyline have the best documented efficacy in the treatment of neuropathic and non-neuropathic pain syndromes [Bryson H M, Wilde M I. Drugs Aging 1996; 8:459-76]. The novel antidepressants bupropion, venlafaxine and duloxetine [Wernicke J, et al., J Pain 2004; 5 (3 suppl 1):S48] have been proven effective in patients with neuropathic pain.

The efficacy of tricyclic antidepressants in the treatment of neuropathic pain appears to be independent of their antidepressant effect and patients with pain but no depression respond to these agents [Max M B, et al., Neurology 1987; 37:589-96]. Although pain reduction occurs at dosages lower than those typically required to treat depression, therapeutic doses are still associated with a number of side effects including drowsiness, dry mouth, blurred vision, constipation, weight gain, low blood pressure after getting up, urinary problems, headaches, impotence, loss of libido, tremor, dizziness, agitation and insomnia.

U.S. Patent Application No. 20040242570 and International PCT Patent Applications WO 03/026563 and WO 2005/092392, which are incorporated by reference as if fully set forth herein, teach conjugates of psychotropic drugs and GABA, for treating psychotropic disorders, proliferative disorders and for enhancing chemosensitization.

SUMMARY OF THE INVENTION

The present inventors have envisioned that conjugates of psychotropic drugs such as anti-depressants and anti-epileptic drugs and organic acids such as GABA agonists would exert an improved therapeutic activity as compared with the psychotropic drug alone and hence could be used in the treatment of pain.

While reducing the present invention to practice, it was indeed found that GABA conjugated antidepressant and anti-epileptic drugs showed synergistic effects as compared to their parent compounds both towards the central perception of pain and the second, peripheral phase of pain. In addition, these conjugates showed an accelerated onset of their protective effects and a longer duration of their protective effects as compared to their parent compounds.

Thus, according to one aspect of the present invention there is provided a method of treating pain, the method comprising administering to a subject in need thereof a therapeutically effective amount of a chemical conjugate which comprises a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se, thereby treating pain. According to one embodiment, the first chemical moiety is an antidepressant or an antiepileptic drug and the second chemical moiety is GABA or R—C(=O)—, where R is an alkyl having 3-5 carbon atoms.

According to another aspect of the present invention there is provided a use of a chemical conjugate comprising a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se, for the manufacture of a medicament for treating pain. According to one embodiment, the first chemical moiety is an antidepressant or an antiepileptic drug and the second chemical moiety is GABA or R—C(=O)—, whereas R is an alkyl having 3-5 carbon atoms.

According to yet another aspect of the present invention there is provided an article-of-manufacture comprising a pharmaceutical composition being packaged in a packaging material and identified in print, in or on the packaging material for use in the treatment of pain, the pharmaceutical composition including a pharmaceutically acceptable carrier and a chemical conjugate which comprises a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se. According to one embodiment, the first chemical moiety is an antidepressant or an antiepileptic drug and the second chemical moiety is GABA or R—C(=O)—, whereas R is an alkyl having 3-5 carbon atoms.

According to an additional aspect of the present invention there is provided a method of treating an addictive disorder, the method comprising administering to a subject in need thereof a therapeutically effective amount of a chemical conjugate which comprises a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se, thereby treating pain. According to one embodiment, the first chemical moiety is an antidepressant or an antiepileptic drug and the second chemical moiety is GABA or R—C(=O)—, whereas R is an alkyl having 3-5 carbon atoms.

According to still an additional aspect of the present invention there is provided a use of a chemical conjugate comprising a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se, for the manufacture of a medicament for treating an addictive disorder. According to one embodiment, the first chemical moiety is an antidepressant or an antiepileptic drug and the second chemical moiety is GABA or R—C(=O)—, whereas R is an alkyl having 3-5 carbon atoms.

According to yet an additional aspect of the present invention there is provided an article-of-manufacture comprising a pharmaceutical composition being packaged in a packaging material and identified in print, in or on the packaging material for use in the treatment of an addictive disorder, the pharmaceutical composition including a pharmaceutically acceptable carrier and a chemical conjugate which comprises a first chemical moiety covalently linked to a second chemical moiety, wherein the first chemical moiety is selected from the group consisting of a psychotropic drug and a GABA agonist and further wherein the second chemical moiety is an organic acid, the organic acid is selected so as to enhance the therapeutic effect induced by the psychotropic drug when the psychotropic drug is administered per se. According to one embodiment, the first chemical moiety is an antidepressant or an antiepileptic drug and the second chemical moiety is GABA or R—C(=O)—, whereas R is an alkyl having 3-5 carbon atoms.

According to further features in embodiments of the invention described below, the second moiety is further selected so as to reduce adverse side effects induced by the psychotropic drug when administered per se.

According to still further features in the described preferred embodiments the second chemical moiety is a GABA agonist.

According to still further features in the described embodiments the second chemical moiety is covalently linked to the first chemical moiety via a bond selected from the group consisting of a carboxylic ester bond, an alkyloxy carboxylic ester bond, an amide bond, an imine bond and a thioester bond.

According to still further features in the described embodiments the psychotropic drug is an antidepressant or an antiepileptic drug.

According to still further features in the described embodiments the antidepressant is selected from the group consisting of a tricyclic antidepressant, a selective serotonin reuptake inhibitor, a serotonin and noradrenaline reuptake inhibitor, a reversible monamine oxidase inhibitor and a monoamine oxidase inhibitor.

According to still further features in the described embodiments the tricyclic antidepressant is a secondary amine tricyclic antidepressant or a tertiary amine tricyclic antidepressant.

According to still further features in the described embodiments the secondary amine tricyclic antidepressant is selected from the group consisting of nortriptyline and desipramine.

According to still further features in the described embodiments the tertiary amine tricyclic antidepressant is selected from the group consisting of amitriptyline and imipramine.

According to still further features in the described embodiments the selective serotonin reuptake inhibitor is selected from the group consisting of fluoxetine, citalopram, paroxetine, fluvoxamine, escitalopram (lexapro) and sertraline.

According to still further features in the described embodiments the serotonin and noradrenaline reuptake inhibitor is venlafaxine.

According to still further features in the described embodiments the reversible monamine oxidase inhibitor is moclobemide.

According to still further features in the described embodiments the monoamine oxidase inhibitor is selected from the group consisting of phenelzine and tranylcypromine.

According to still further features in the described embodiments the antiepileptic drug is selected from the group consisting of carbamazepine, valproate, ethosuximide and phenyloin.

According to still further features in the described embodiments the antidepressant drug is selected from the group consisting of venlafaxine, duloxetine and bupropion.

According to still further features in the described embodiments the psychotropic drug is selected from the group consisting of nortryptiline, fluoxetine and valproic acid.

According to still further features in the described embodiments the first chemical moiety is a GABA agonist.

According to still further features in the described embodiments the second chemical moiety is a GABA agonist.

According to still further features in the described embodiments the GABA agonist is selected from the group consisting of (±) baclofen, γ-aminobutyric acid (GABA), γ-hydroxybutyric acid, aminooxyacetic acid, β-(4-chlorophenyl)-γ-aminobutyric acid, isonipecotic acid, piperidine-4-sulfonic acid, 3-aminopropylphosphonous acid, 3-aminopropylphosphinic acid, 3-(aminopropyl)methylphosphinic acid, 1-(aminomethyl)cyclohexaneacetic acid (gabapentin), y-vinyl-γ-aminobutyric acid (4-aminohex-5-enoic acid, y-vinyl GABA, vigabatrin) and 3-(2-imidazolyl)-4-aminobutanoic acid.

According to still further features in the described embodiments the organic acid has a general formula:

—R—C(=O)— wherein,

R is selected from the group consisting of a substituted or non-substituted hydrocarbon having 1-20 carbon atoms, a substituted or non-substituted hydrocarbon having 1-20 carbon atoms and at least one heteroatom selected from the group consisting of oxygen, nitrogen and sulfur and $R_1$, whereas, $R_1$ is a moiety of a general formula:

—Z—C(=O)O—CHR$_2$—R$_3$ wherein,

Z is selected from the group consisting of a single bond, a substituted or non-substituted hydrocarbon having 1-20 carbon atoms and a substituted or non-substituted hydrocarbon having 1-20 carbon atoms and at least one heteroatom selected from the group consisting of oxygen, nitrogen and sulfur;

$R_2$ is selected from the group consisting of hydrogen and an alkyl having 1-10 carbon atoms; and $R_3$ is selected form the group consisting of hydrogen, a substituted or non-substituted hydrocarbon having 1-20 carbon atoms and a substituted or non-substituted alkyl having 1-20 carbon atoms and at least one heteroatom selected from the group consisting of oxygen, nitrogen and sulfur.

According to still further features in the described embodiments R is a substituted or non-substituted alkyl having 3-5 carbon atoms.

Exemplary conjugates according to the present embodiments include, without limitation, GABAoxymethylGABA (also referred to herein as AN-214), GABA-oxymethylvalproate (also referred to herein as AN-216), fluoxetine-GABA (also referred to herein as AN-227) and nortriptyline-GABA (also referred to herein as AN-228).

According to still further features in the described embodiments the pain is a chronic pain.

According to still further features in the described embodiments the chronic pain is a neuropathic pain or a nociceptive pain.

According to still further features in the described embodiments the pain is an acute pain.

According to still further features in the described embodiments the addictive disorder is alcoholism and/or smoking.

According to a further aspect of the present invention there is provided a chemical conjugate comprising a first chemical moiety covalently linked to a second chemical moiety, wherein each of the chemical moieties is independently a GABA agonist.

According to a further aspect of the present invention there is provided a pharmaceutical composition comprising, as an active ingredient, the chemical conjugate comprising a first chemical moiety covalently linked to a second chemical moiety, wherein each of the chemical moieties is independently a GABA agonist and a pharmaceutically acceptable carrier.

According to yet a further aspect of the present invention there is provided a method of treating a CNS disease or disorder, the method comprising administering to a subject in need thereof a therapeutically effective amount of the chemical conjugate comprising a first chemical moiety covalently linked to a second chemical moiety, wherein each of the chemical moieties is independently a GABA agonist.

According to still a further aspect of the present invention there is provided a use of the conjugate comprising a first chemical moiety covalently linked to a second chemical moiety, wherein each of the chemical moieties is independently a GABA agonist, for the preparation of a medicament.

According to further features in embodiments of the invention described below, the GABA agonists are covalently linked therebetween via a bond selected from the group consisting of a carboxylic ester bond, an alkyloxy carboxylic ester bond, an amide bond, an imine bond and a thioester bond.

According to still further features in the described embodiments the bond is an alkyloxy carboxylic ester bond.

According to still further features in the described embodiments each of the GABA agonists is independently selected from the group consisting of (±) baclofen, γ-aminobutyric acid (GABA), γ-hydroxybutyric acid, aminooxyacetic acid, β-(4-chlorophenyl)-γ-aminobutyric acid, isonipecotic acid, piperidine-4-sulfonic acid, 3-aminopropylphosphonous acid, 3-aminopropylphosphinic acid, 3-(aminopropyl)methylphosphinic acid, 1-(aminomethyl)cyclohexaneacetic acid (gabapentin), y-vinyl-γ-aminobutyric acid (4-aminohex-5-enoic acid, y-vinyl GABA, vigabatrin), vigabatrin) and 3-(2-imidazolyl)-4-aminobutanoic acid.

According to still further features in the described embodiments each of the GABA agonists is a γ-aminobutyric acid (GABA).

According to still further features in the described embodiments the pharmaceutical composition comprising, as an active ingredient, the chemical conjugate comprising a first chemical moiety covalently linked to a second chemical moiety, wherein each of the chemical moieties is independently a GABA agonist and a pharmaceutically acceptable carrier, is packaged in a packaging material and identified in print, on or in the packaging material, for use in the treatment of a CNS disease or disorder.

According to still further features in the described embodiments the medicament is for treating a CNS disease or disorder.

According to still further features in the described embodiments the CNS disease or disorder is selected from the group consisting of a pain disorder, a motion disorder, a dissociative disorder, a mood disorder, an affective disorder, a neurodegenerative disease or disorder and a convulsive disorder.

According to still further features in the described embodiments the CNS disease or disorder is selected from the group consisting of Parkinson's, Multiple Sclerosis, Huntington's disease, action tremors and tardive dyskinesia, panic, anxiety, depression, alcoholism, insomnia and manic behavior, Alzheimer's and epilepsy.

The present invention thus provides a novel method for treating pain, and particularly neuropathic pain, which is characterized by superior efficacy and reduced side effects as compared to the presently known medications. The present invention further provides novel conjugates which can be used in the treatment of pain, as well as other CNS diseases and disorders.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "about" refers to ±10%.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
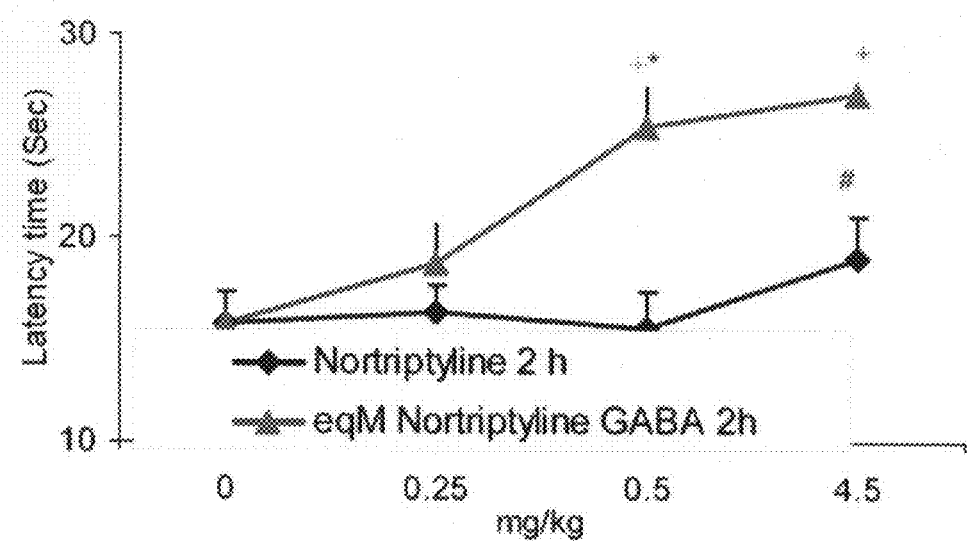

FIG. 1 presents comparative dose response plots illustrating the latency of nociceptive reaction to heat of mice treated p.o. with nortriptyline and equimolar dose of nortriptyline-GABA conjugate (AN-228). Male Balb-c mice (6/group) were treated p.o. with the indicated doses of nortriptyline, respective equimolar doses nortriptyline-GABA conjugate or vehicle. Two hours later the animals were placed on the surface of the hot-plate (52±0.2° C.). Response to the heat, manifested by shaking or licking of the paws or jumping, was recorded as the index of response latency.

Figure 2A:
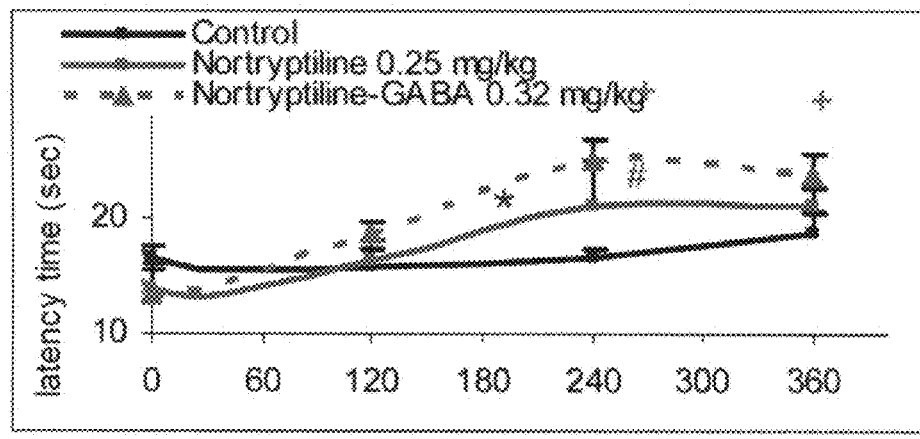
Figure 2B:
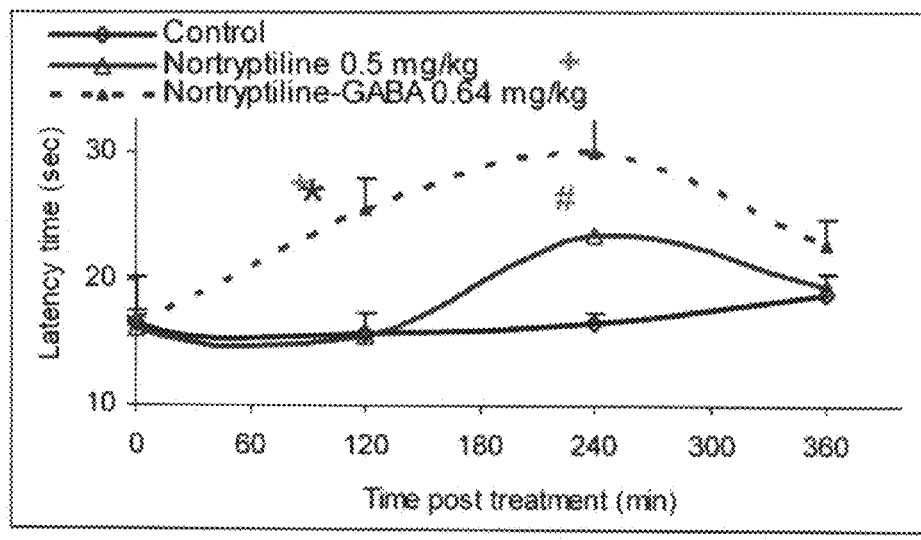

FIGS. 2A-B present plots illustrating the time-course of latency of the nociceptive reaction to heat of mice treated with nortriptyline and the respective equimolar doses of the conjugate nortriptyline-GABA (AN-228). In FIG. 2A, male Balb-c mice were treated p.o. with 0.25 mg/kg nortriptyline, equimolar dose of its GABA conjugate (0.32 mg/kg) or vehicle. In FIG. 2B, male Balb-c mice were treated p.o. with 0.5 mg/kg nortriptyline, equimolar dose of its GABA conjugate (0.64 mg/kg) or vehicle. Six mice were used in all experimental groups. The animals latency response to heat (sec), using a hot plate at 52±0.2° C., was measured before and after treatment as indicated.

Figure 3A:
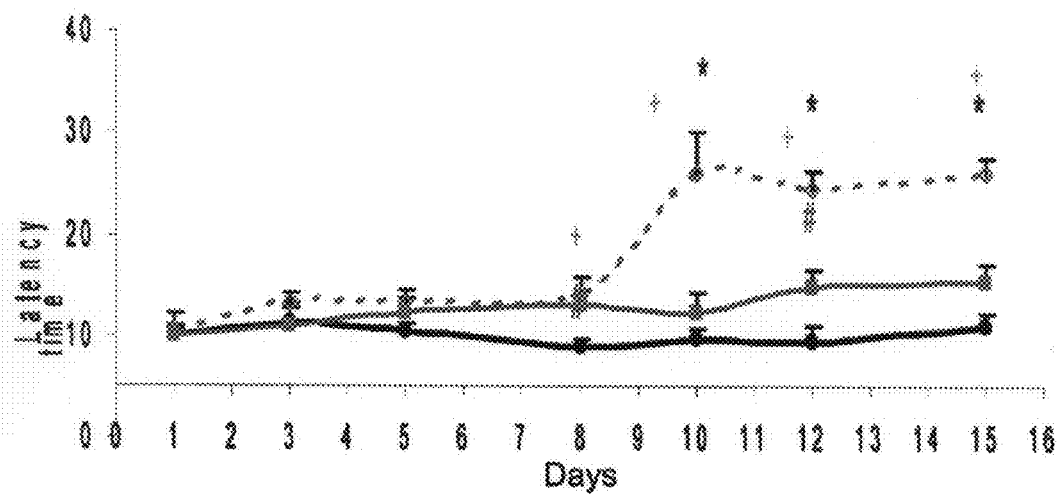
Figure 3B:
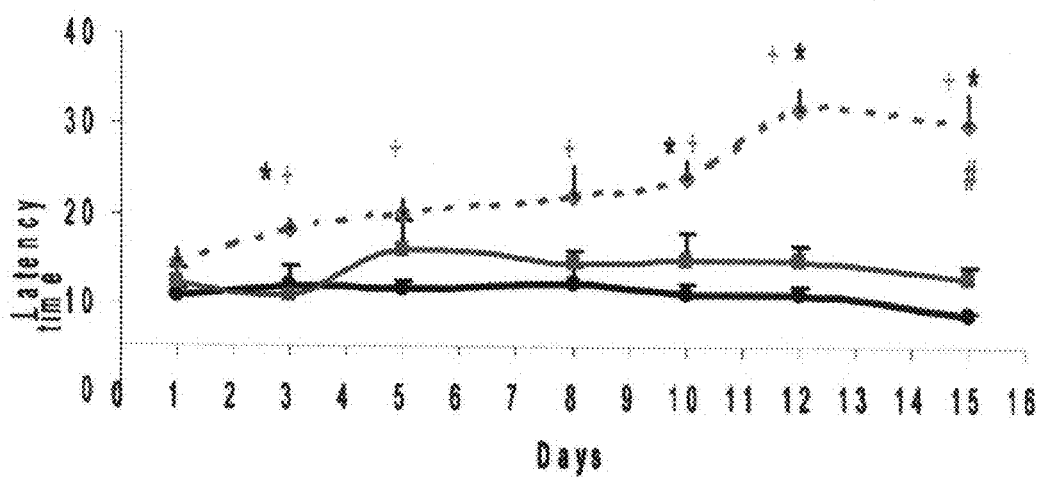
Figure 3C:
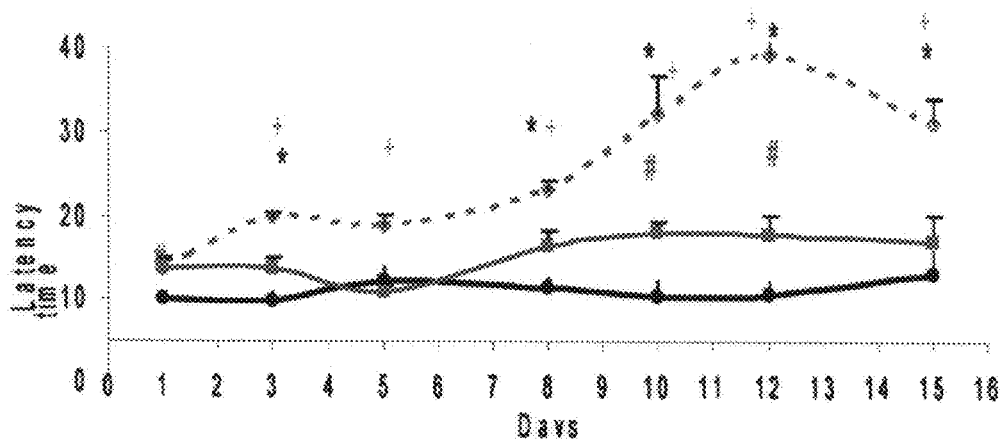
Figure 3D:
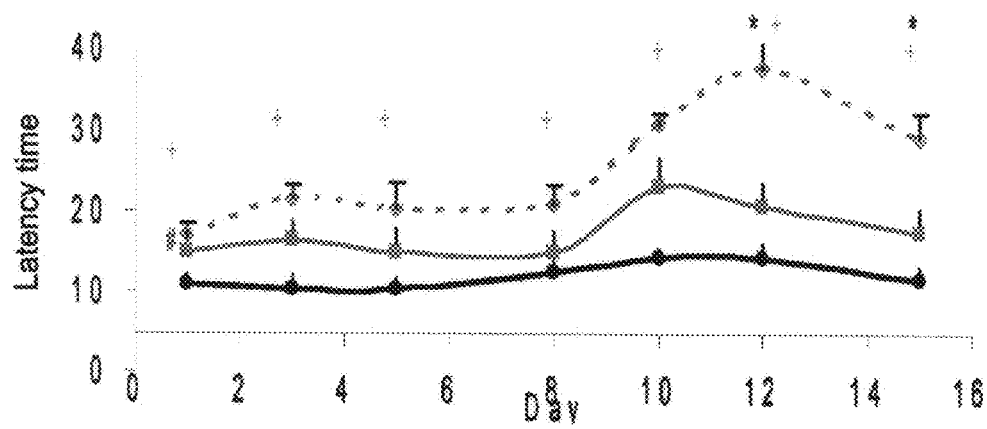
Figure 3E:
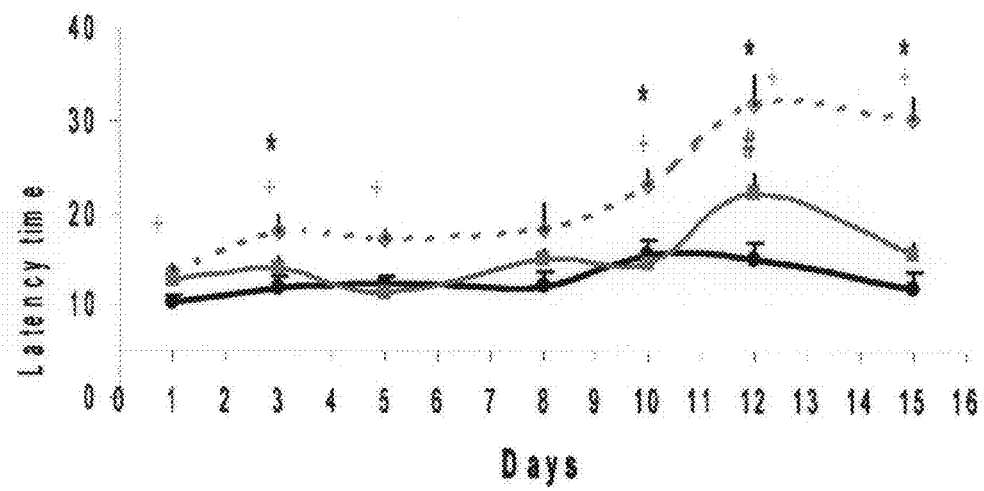

FIGS. 3A-E present graphs illustrating the effect of chronic administration of nortriptyline (0.2 mg/kg) and an equimolar dose of its GABA conjugate (AN-228) on latency of the nociceptive reaction to heat. The latency of the nociceptive reaction was measured prior to treatment (FIG. 3A); two hours following treatment (FIG. 3B); three hours following treatment (FIG. 3C); four hours following treatment (FIG. 3D); and five hours following treatment (FIG. 3E).

FIG. 4 presents a graph illustrating the effect on latency of the nociceptive reaction to heat of fluoxetine, equimolar GABA and equimolar fluoxetine-GABA conjugate (AN-227). Male Balb-c mice were placed on the surface of the hot-plate and the time between the animal placement and its response was recorded as the index of response latency. The reaction was recorded at: −60, 0, 60, 120, 180, 240, 300 min after p.o. administration of vehicle (n=18); fluoxetine 10 mg/kg (n=11); equimolar fluoxetine-GABA conjugate (n=11); and equimolar GABA (n=8).

Figure 5A:
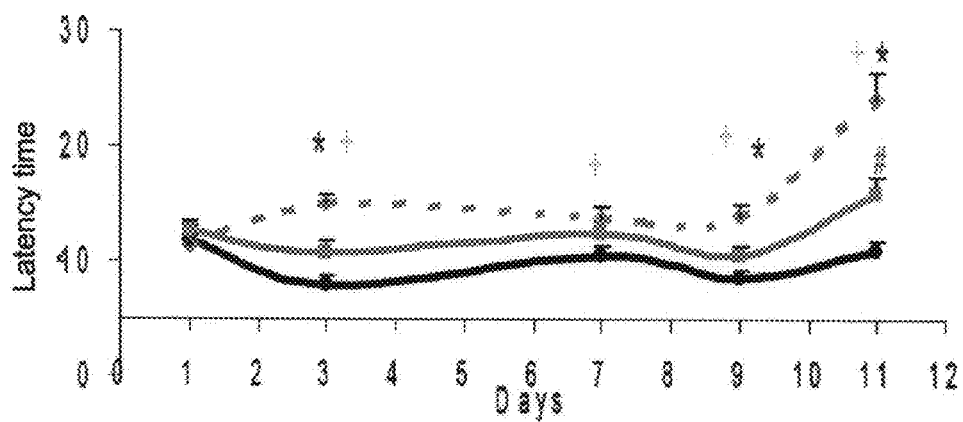
Figure 5B:
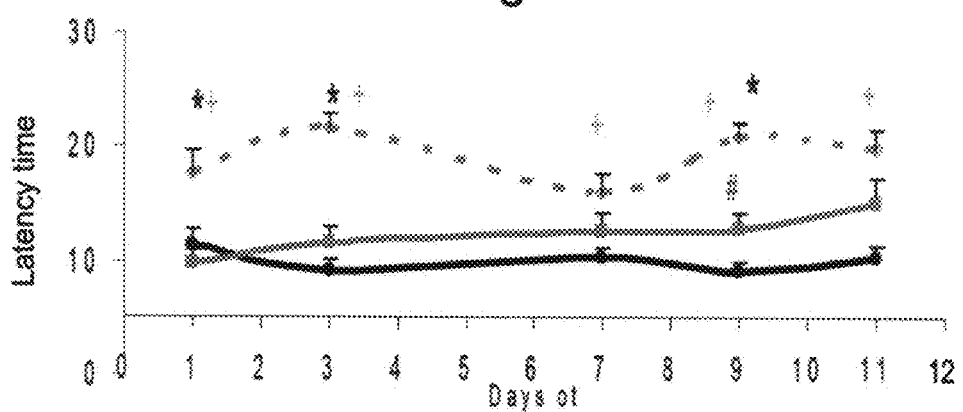
Figure 5C:
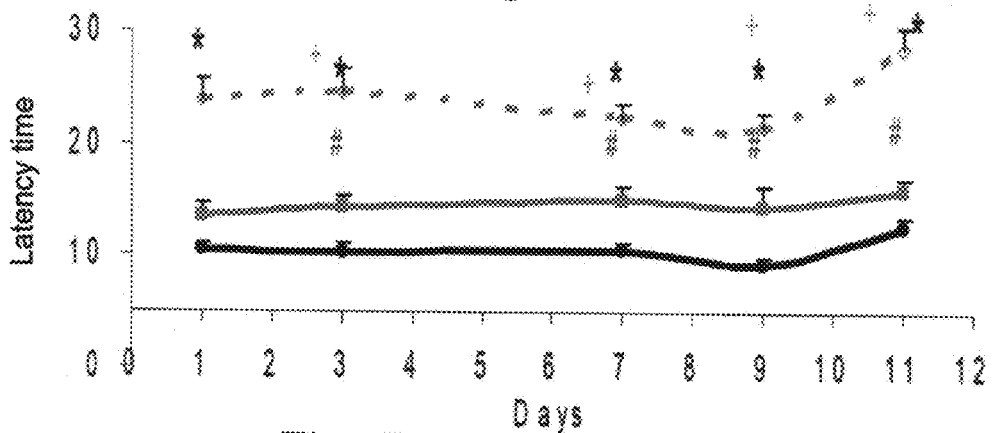
Figure 5D:
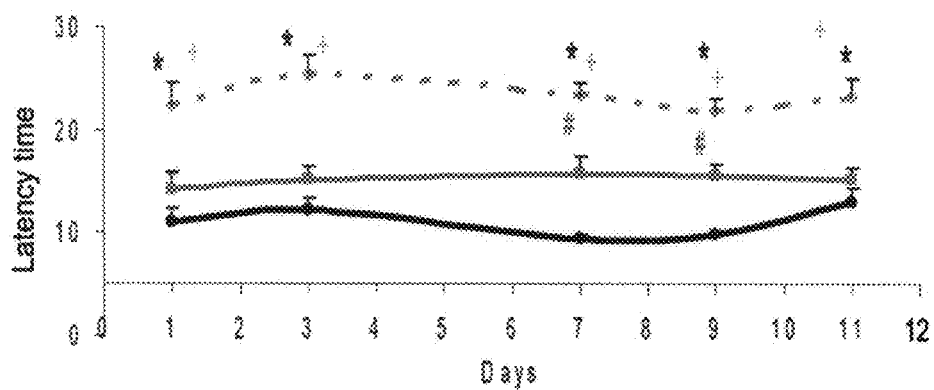
Figure 5E:
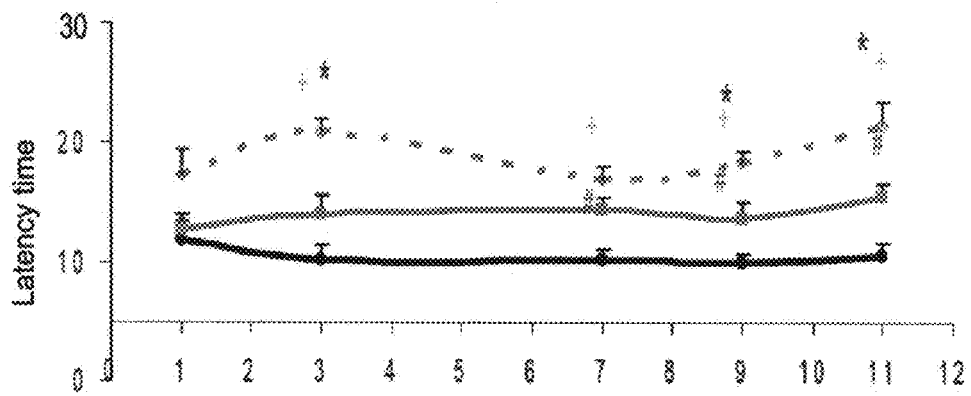

FIGS. 5A-E present graphs illustrating the effect of chronic administration (p.o.) of fluoxetine (10 mg/kg) and an equimolar does of its GABA conjugate (AN-227) on latency of the nociceptive reaction to heat. Male Balb-c mice (n=11 per treatment groups and n=10 of control) were treated five times a week for 2 weeks. The latency of the nociceptive reaction was measured prior to treatment (FIG. 5A); two hours following treatment (FIG. 5B); three hours following treatment (FIG. 5C); four hours following treatment (FIG. 5D); and five hours following treatment (FIG. 5E).

Figure 6:
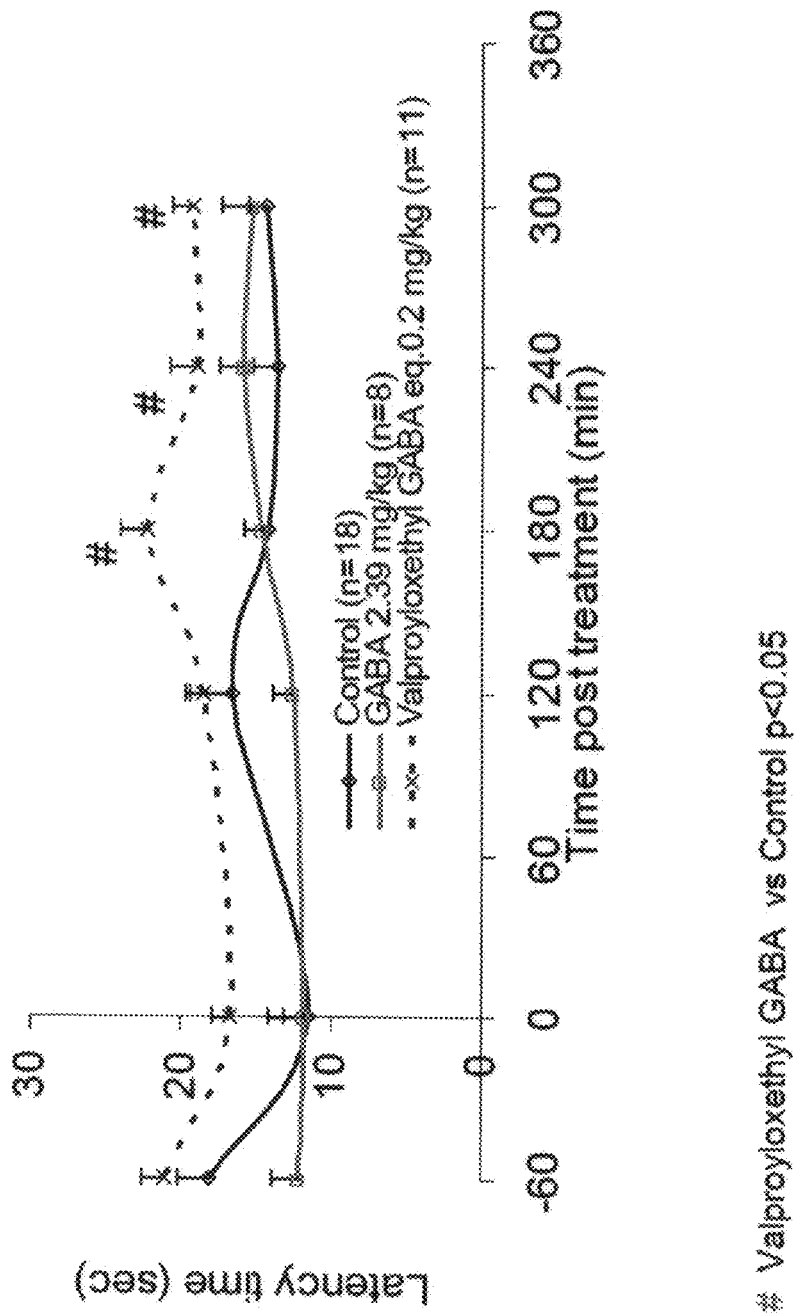
Figure 7A:
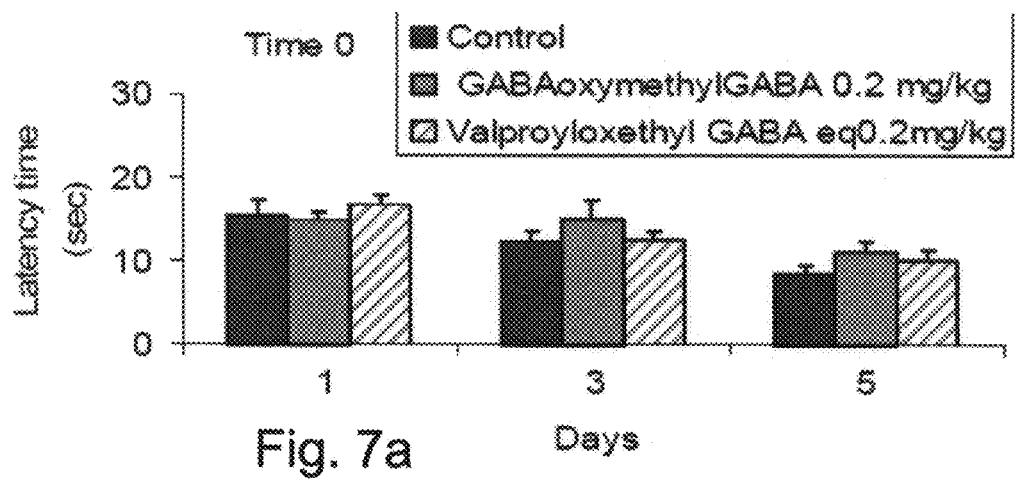
Figure 7B:
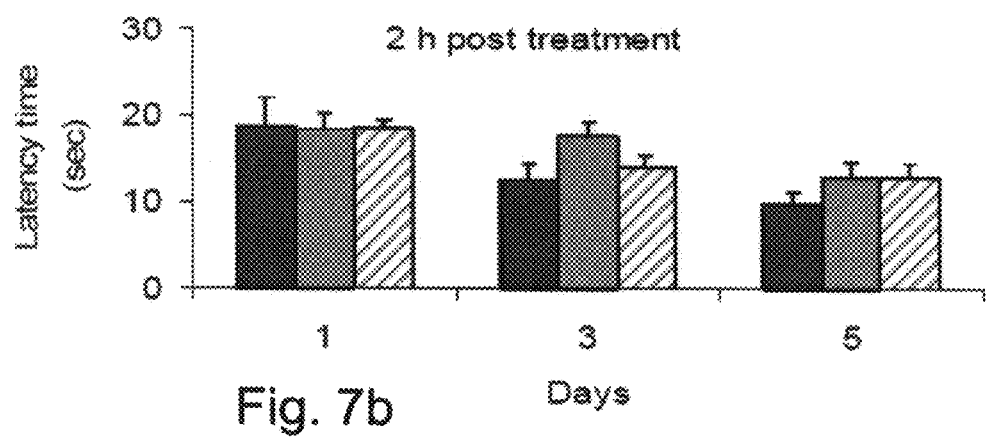
Figure 7C:
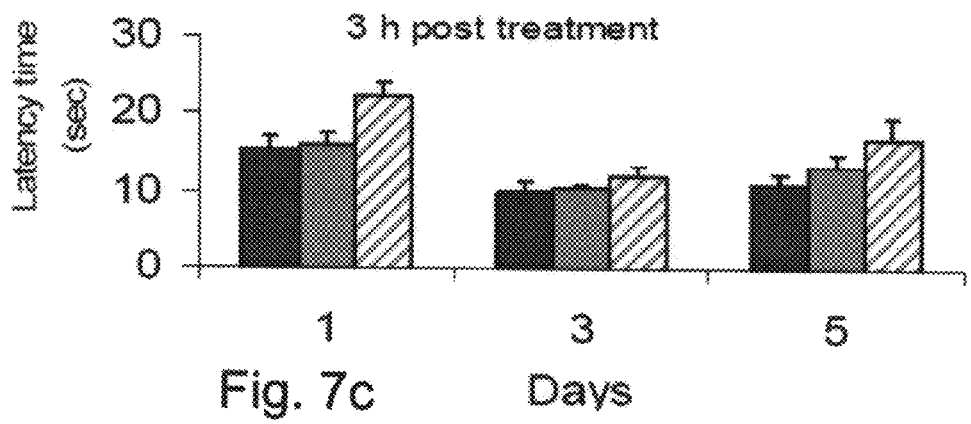
Figure 7D:
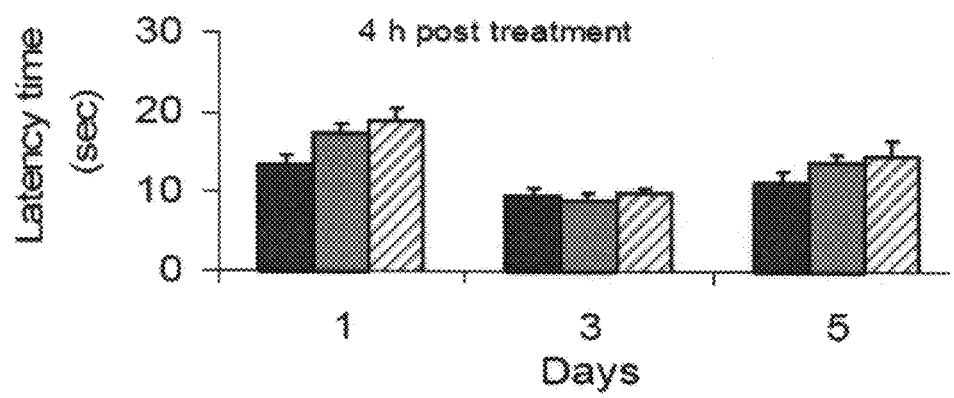
Figure 7E:
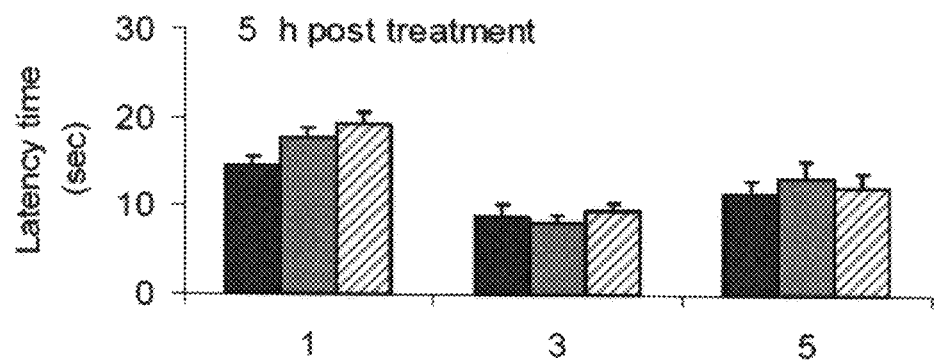

FIG. 6 presents a graph illustrating the effect of GABA-oxymethylvalproate (AN-216) 0.24 mg/kg and an equimolar dose of GABA (2.39 mg/kg) on heat sensation-time course. The latency response to heat was recorded at: −60, 0, 60, 120, 180, 240 and 300 min, following treatment.

FIGS. 7A-E present graphs illustrating the effect of five day treatment of GABA-oxymethylGABA (AN-214) 0.2 mg/kg (n=11) and an equimolar dose of GABA-oxymethylvalproate (AN-216) (n=8) on latency of the nociceptive reaction to heat. The latency of the nociceptive reaction was measured prior to treatment (FIG. 7A); two hours following treatment (FIG. 7B); three hours following treatment (FIG. 7C); four hours following treatment (FIG. 7D); and five hours following treatment (FIG. 7E) on days 1, 3 and 5.

Figure 8A:
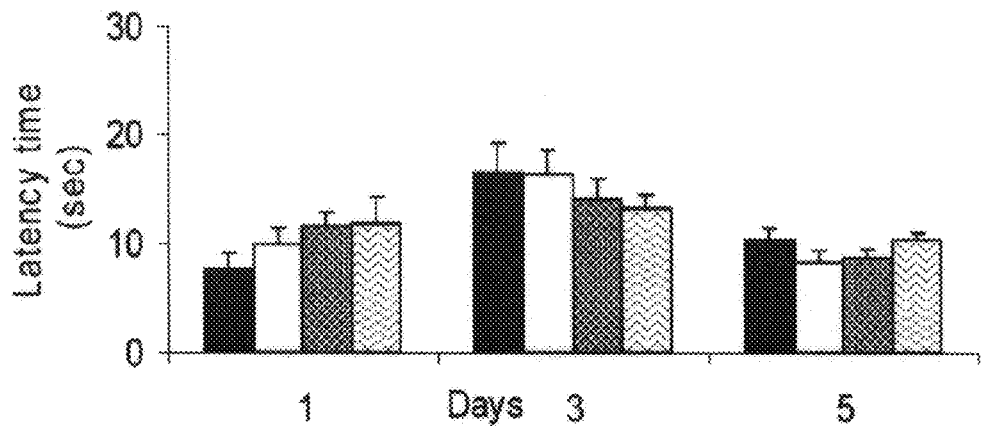
Figure 8B:
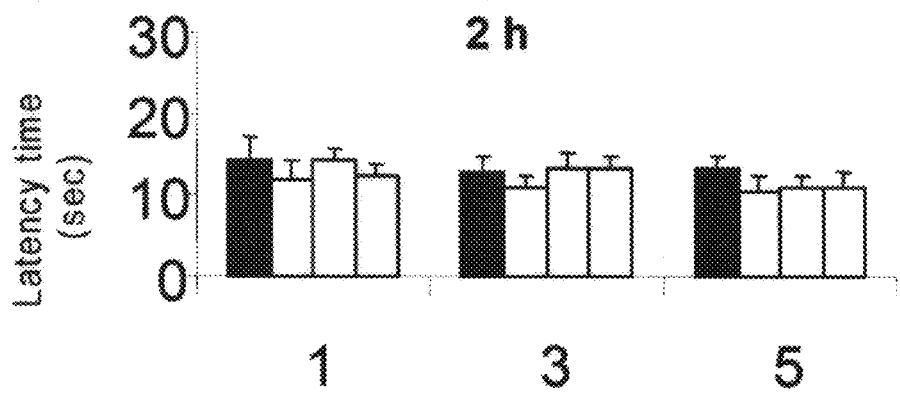
Figure 8C:
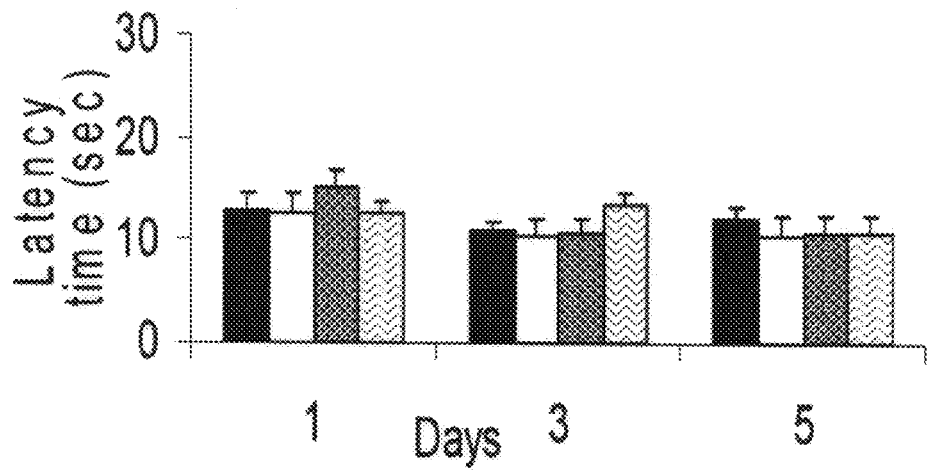
Figure 8D:
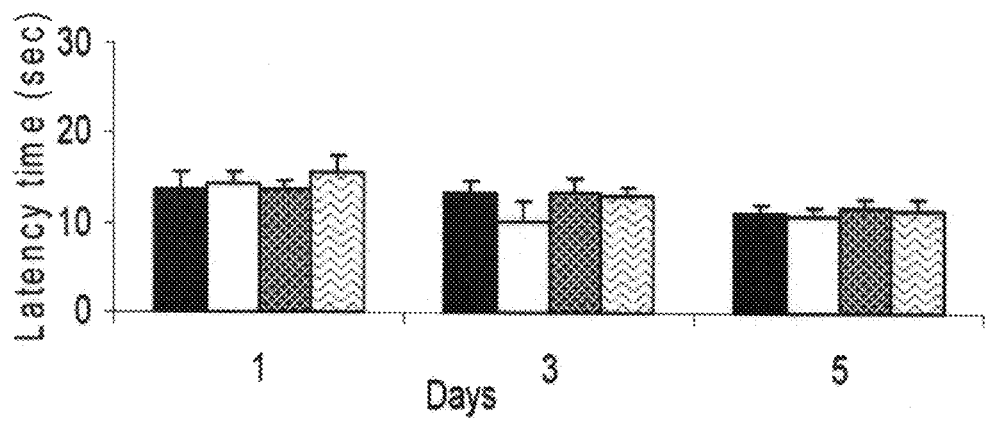
Figure 8E:
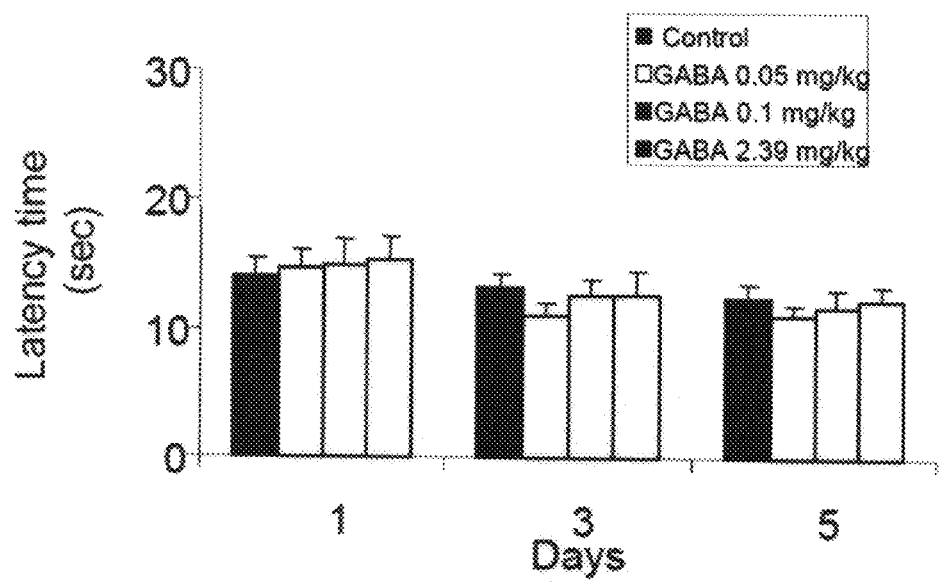

FIGS. 8A-E present graphs illustrating the effect of five day treatment of GABA on latency of the nociceptive reaction to heat. Male Balb-c mice (n=8/group) were treated with the indicated doses of GABA daily for five days. The latency of the nociceptive reaction was measured prior to treatment (FIG. 8A); two hours following treatment (FIG. 8B); three hours following treatment (FIG. 8C); four hours following treatment (FIG. 8D); and five hours following treatment (FIG. 8E).

Figure 9A:
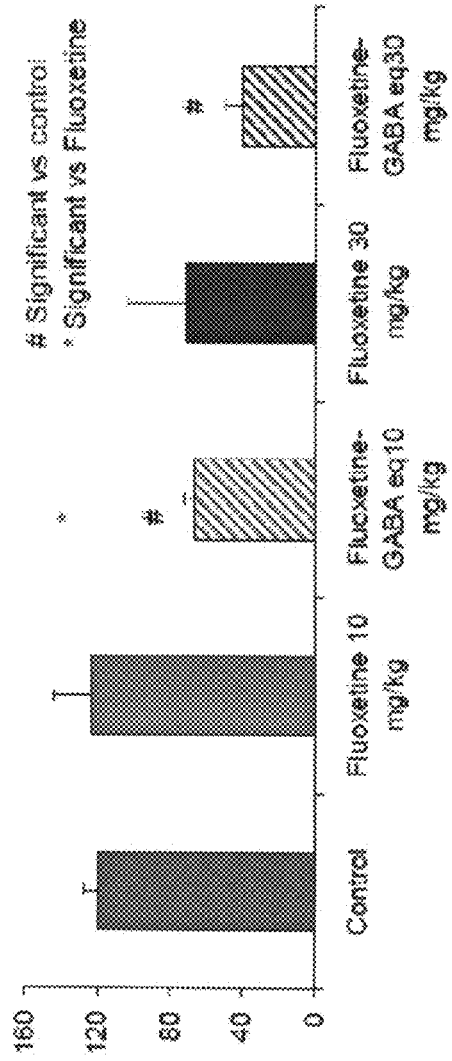
Figure 9B:
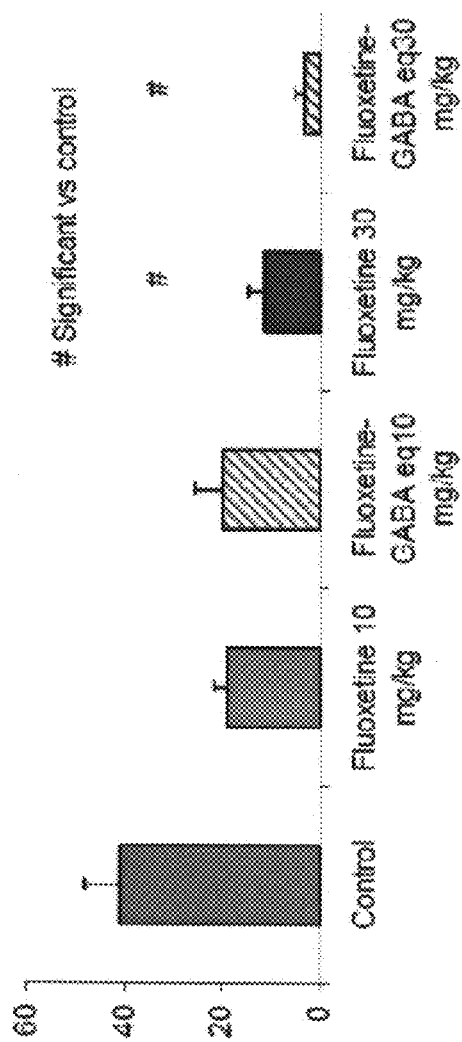

FIGS. 9A-B present graphs illustrating the pain relieving effect of fluoxetine and the fluoxetine-GABA conjugate (AN-227) on both the early neurogenic phase—and the late inflammatory peripheral phase to pain as measured by a formalin test. Balb/c mice (5/group) were treated with: vehicle (DDW), 10 mg/kg fluoxetine, 30 mg/kg fluoxetine and their respective equimolar doses of fluoxetine-GABA conjugate. Three hours later 1% (20 ml) formalin was injected to intraplantar of the right hind paw. Immediately after injection, the mouse was placed in a Plexiglas chamber for observation. The amount of time the animal spent licking the injected paw was recorded as a quantitative indication of nociception. (A) The early neurogenic phase (nociceptive response) was measured between 0-5 min and (B) the late phase from 20-30 min after formalin injection (nociceptors and inflammatory nociceptive responses).

Figure 10A:
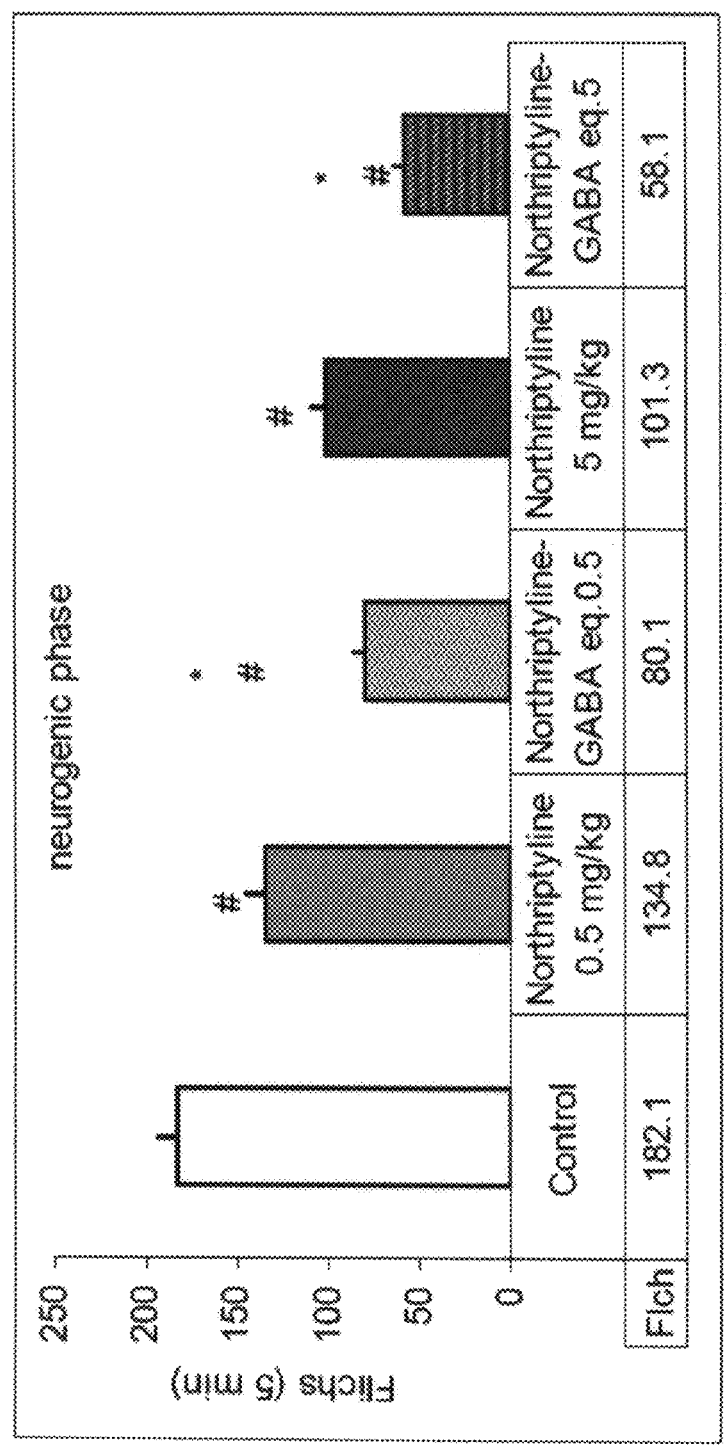
Figure 10B:
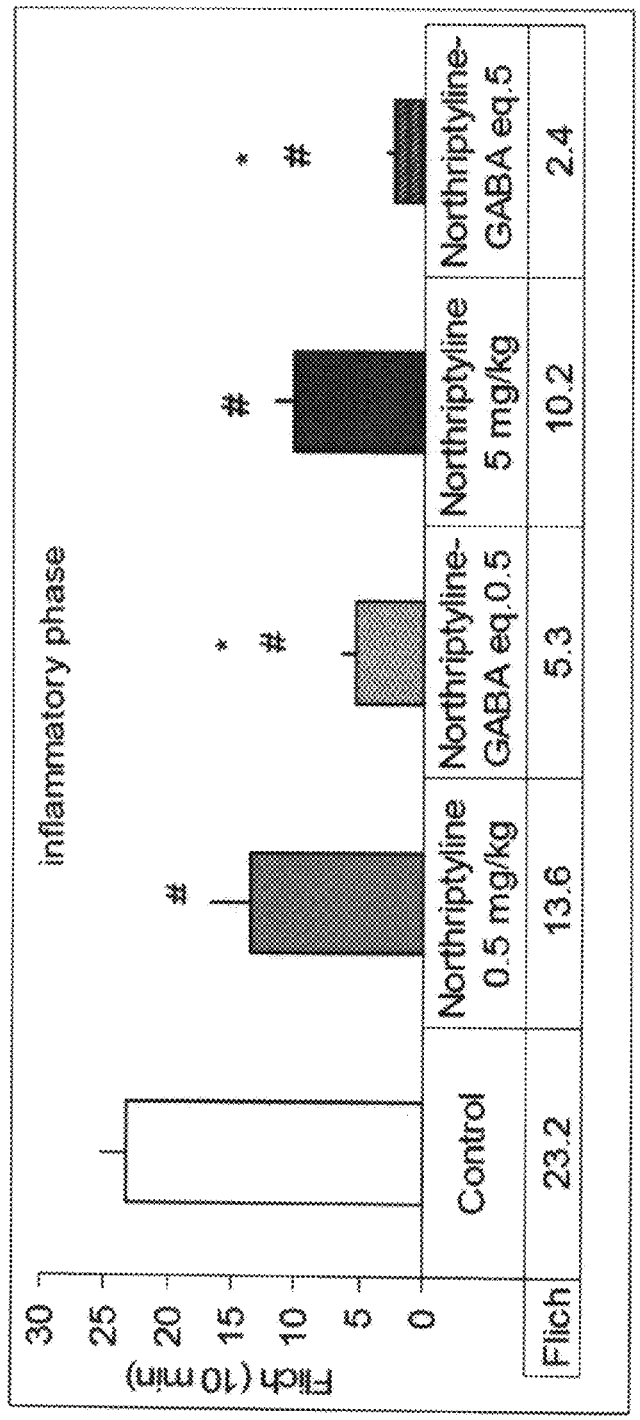

FIGS. 10A-B present graphs illustrating the pain relieving effect of nortriptyline and the nortriptyline-GABA conjugate (AN-228) on both the early neurogenic phase—and the late inflammatory peripheral phase to pain as measured by a formalin test. Balb/c mice (5/group) were treated with: vehicle (DDW), 0.5 mg/kg nortriptyline, 5 mg/kg nortriptyline and their respective equimolar doses of nortriptyline-GABA conjugate. Three hours later 1% (20 µl) formalin was injected to intraplantar of the right hind paw. Immediately after injection, the mouse was placed in a Plexiglas chamber for observation. The amount of time the animal spent licking the injected paw was recorded as a quantitative indication of nociception. (A) The early neurogenic phase (nociceptive response) was measured between 0-5 min and (B) the late phase from 10 min after formalin injection (nociceptors and inflammatory nociceptive responses). The results are an average of two experiments.

Figure 11:
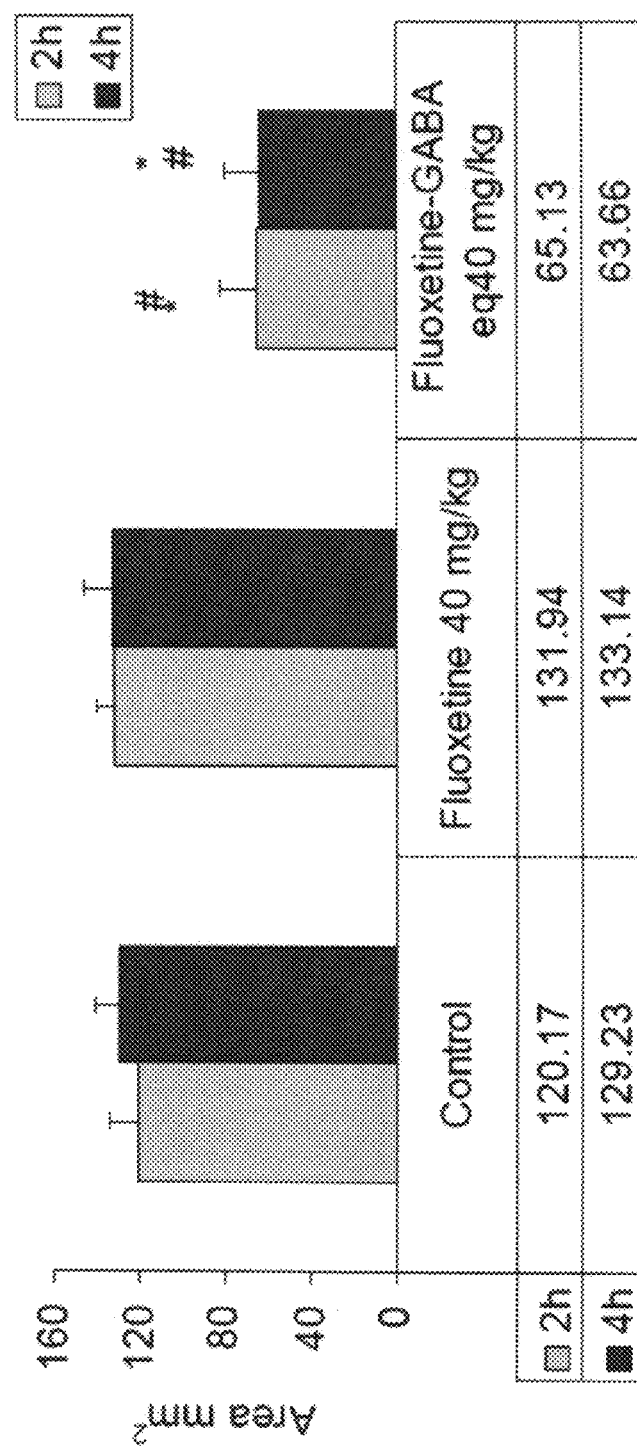

FIG. 11 presents a graph illustrating the anti-inflammatory effect of fluoxetine and the fluoxetine-GABA conjugate (AN-227) as measured by a carrageenan-induced paw edema test. Wistar rats (250-350 g) were treated p.o. with fluoxetine 40 mg/kg (n=8), equimolar of fluoxetine-GABA conjugate (n=6) and vehicle (n=8). After 3 h they were injected to the plantar surface of the left hind paw with 100 µl 1% solution of λ-carrageenan. The edema developed in the injected area was measured 2 and 4 h later with caliper.

Figure 12:
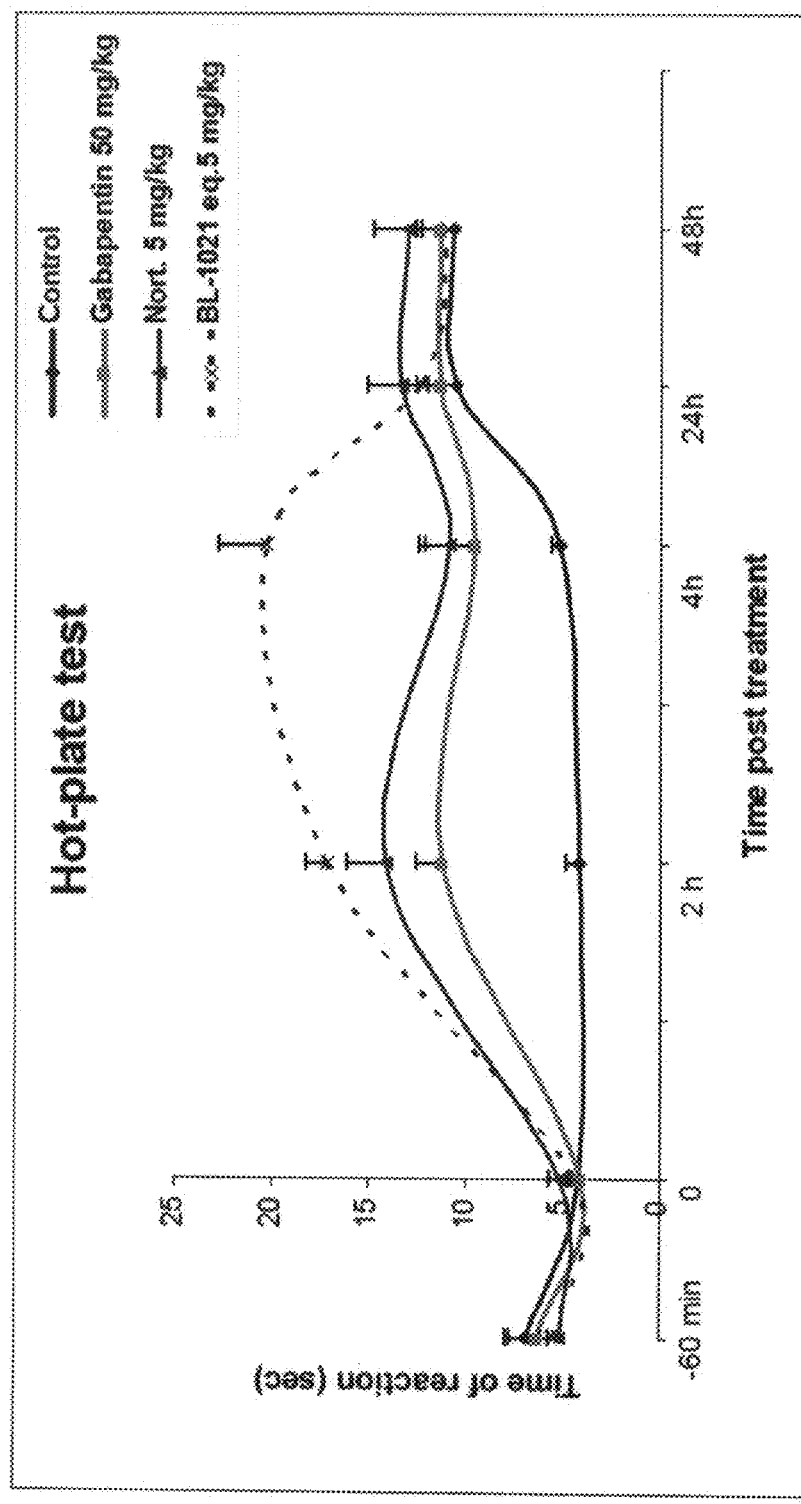

FIG. 12 is a graph illustrating the effect of treatment with Nortriptyline-GABA (AN-228) on latency of the nociceptive reaction to heat as compared to Nortriptyline alone and Gabapentin (1-(aminomethyl)cyclohexaneacetic acid) 2-48 hours following injection.

FIGS. 13A-B are bar graphs illustrating the effect of treatment with Nortriptyline-GABA (AN-228) on paw height as compared to Nortriptyline alone and control (FIG. 13A) and as compared to Nortriptyline alone, control and Gabapentin (FIG. 13B) at particular time points following injection.

FIGS. 14A-B are bar graphs illustrating the effect of treatment with Nortriptyline-GABA (AN-228) as compared to Nortriptyline alone, control, Gabapentin and a mixture of Nortriptyline and GABA on INF-γ secretion (FIG. 14A) and TNF-α secretion (FIG. 14B).

DESCRIPTION OF THE PREFERRED EMBODIMENTS

The present invention is of a novel use of conjugates of psychotropic drugs, particularly antidepressants and anti-epileptic drugs, and organic acids such as GABA, for the treatment of pain. The present invention is further of novel conjugates of GABA agonists and their use in the treatment of CNS diseases and disorders (e.g., pain).

The principles and operation of the chemical conjugates according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Psychotropic drugs are often encumbered by short and long term adverse side effects. Conjugation thereof with GABA agonists results in their enhanced therapeutic activity and a substantial reduction of induced adverse side effects. Thus, U.S. Patent Application No. 20040242570 and International PCT Patent Applications WO 03/026563 and WO 2005/092392, by the present inventors, teach GABA-conjugated psychotropic drugs for treating psychotropic disorders, proliferative disorders and for enhancing chemosensitization.

Whilst conceiving the present invention, it was hypothesized that conjugates of organic acids such as GABA and antidepressants and anti-epileptics may not only enhance the respective antidepressant and antiepileptic therapeutic properties of these drugs, but may also improve other characteristics thereof, such as their pain relieving capabilities. Thus, as demonstrated in Examples 2 and 3, GABA conjugated antidepressant and antiepileptic drugs unexpectedly showed synergistic effects as compared to their parent compounds both towards the central perception of pain and the second, peripheral phase of pain. Not only did the GABA conjugated drugs show enhanced pain relieving effects, but they also showed an accelerated onset of their protective effects and a longer duration of their protective effects as compared to their non-GABA conjugated counterparts.

Without being bound to any particular theory, it is believed that the enhanced palliative activities of the conjugates are due to the simultaneous action of the psychotropic drug and the organic acid at the same site in the brain resulting in a synergistic pain relief. In addition, conjugation is believed to improve brain permeability of both chemical moieties.

Thus, according to one aspect of the present invention, there is provided a method of treating pain, which is effected by administering to a subject in need thereof a therapeutically effective amount of a chemical conjugate. The chemical conjugate includes a first chemical moiety that is covalently linked to a second chemical moiety. The first chemical moiety may be a psychotropic drug or a GABA agonist, whereas the second chemical moiety is an organic acid, selected so as to enhance the therapeutic efficacy of the psychotropic drug and/or to reduce side effects induced by the psychotropic drug when administered per se.

By "administered per se" it is meant that a non-conjugated psychotropic drug, corresponding to the same psychotropic drug that constitutes the first moiety in the conjugate, is utilized. Thus, the conjugates described herein are such that the therapeutic efficacy thereof is enhanced as compared to the therapeutic efficacy of a corresponding non-conjugated psychotropic drug and/or the side effects induced thereby are reduced as compared to a corresponding non-conjugated psychotropic drug.

As used herein, the term "pain" encompasses both acute and chronic pain. As used herein, the term "acute pain" means immediate, generally high threshold, pain brought about by injury such as a cut, crush, burn, or by chemical stimulation such as that experienced upon exposure to capsaicin, the active ingredient in chili peppers. The term "chronic pain," as used herein, means pain other than acute pain and includes, without limitation, neuropathic pain, visceral pain, fibromyalgia pain, inflammatory pain, headache pain, muscle pain and referred pain. It is understood that chronic pain often is of relatively long duration, for example, months or years and can be continuous or intermittent.

In one embodiment, the conjugates of the present invention are used to treat "neuropathic pain," which, as used herein, means pain resulting from injury to a nerve. Neuropathic pain can be distinguished from nociceptive pain, which is pain caused by acute tissue injury involving small cutaneous nerves or small nerves in muscle or connective tissue. In contrast to neuropathic pain, nociceptive pain usually is limited in duration to the period of tissue repair and usually can be alleviated by available analgesic agents or opioids [Myers, Regional Anesthesia 20:173-184 (1995)].

Neuropathic pain typically is long-lasting or chronic and can develop days or months following an initial acute tissue injury. Neuropathic pain can involve persistent, spontaneous pain, as well as allodynia, which is a painful response to a stimulus that normally is not painful, or hyperalgesia, an accentuated response to a painful stimulus that usually is trivial, such as a pin prick. Neuropathic pain generally is resistant to opioid therapy [Myers, (1995) supra].

As used herein, the term "chemical moiety" refers to a moiety derived from a chemical compound, which retains its functionality.

Herein throughout, whenever a chemical moiety is described, it is to be understood as that part of the chemical moiety that is linked to the other chemical moiety in the conjugate, unless otherwise indicated.

Thus, the phrase "psychotropic drug", whenever used with respect to the first moiety in the conjugate, refers to a major portion of a psychotropic drug that is covalently linked to another chemical moiety, as this term is defined hereinabove.

As is described hereinabove, the phrase "psychotropic drug" encompasses any agent or drug that exerts an activity in the central nervous system and thereby can be used in the treatment of various central nervous system diseases or disorders.

Hence, psychotropic drugs, according to the present invention, include, for example, moieties derived from anxiolytic drugs such as, but not limited to, benzodiazepines, phenothiazines and butyrophenones, MAO inhibitors, anti-depressants, anti-epileptic drugs, anti-convulsive drugs (also referred to as anti-convulsants), anti-parkinsonian drugs, and acetylcholine esterase inhibitors. The psychotropic drugs can be tricyclic, bicyclic or monocyclic.

Preferred psychotropic drugs, according to the present invention, are those having an amine group, a thiol group or a hydroxyl group, as these terms are defined hereinbelow, which can be reacted with the organic acid or a reactive derivative thereof. Such groups can be present in the psychotropic drug, prior to its incorporation in the conjugate, either as a free functional group or as a part of another functional group, e.g., an amide group, a carboxylic acid group and the like, as these terms are defined hereinbelow.

According to a preferred embodiment of the present invention, the psychotropic drug from which the first chemical moiety is derived is known for its therapeutic effect on pain, e.g., antidepressant or antiepileptic drugs. Both antidepressants and antiepileptics have been shown to be efficacious in the treatment of pain and more specifically neuropathic pain.

As used herein, the phrase "antidepressant drug" refers to any drug which is known to alleviate the causes and/or symptoms of depression regardless of its mechanism of action.

The phrase "anti-epileptic drug", which is also referred to herein and in the art as "anti-epileptic", "anti-convulsant" or "anti-convulsive drug", describes any drug which is known to alleviate the causes and/or symptoms of convulsions and particularly, convulsions caused by epilepsy.

As illustrated in the Examples section that follows, conjugates of various psychotropic drugs have been tested and were shown to exert enhanced therapeutic activity as compared to the respective non-conjugates drugs, regardless of the pathway affected thereby or of the receptor interacted therewith. Thus, for example, it is demonstrated that conjugates of two known antidepressants, fluoxetine and nortriptyline, acting on two entirely separate pathways (selective serotonin reuptake inhibitor and selective norepinephrine reuptake inhibitor, respectively) were shown to induce pain relief in mouse in vivo studies.

In addition, a known antiepileptic drug (valproic acid) acting on a GABA pathway was also shown to be effective in the relief of pain. It is suggested that since valproic acid is a drug that is capable of crossing the BBB, a valproate-GABA conjugate (e.g., GABA-oxymethylvalproate) may carry the GABA into the brain and the GABA in turn could potentiate the activity of valproic acid.

Thus, according to this aspect of the present invention, the antidepressant drug may be a tricyclic antidepressant (e.g. secondary amine tricyclic antidepressant or a tertiary amine tricyclic antidepressant), a selective serotonin reuptake inhibitor, a serotonin and noradrenaline reuptake inhibitor, a reversible monamine oxidase inhibitor and a monamine oxidase inhibitor.

Non-limiting examples of antidepressants include nortriptyline, desipramine, amitriptyline, imipramine, fluoxetine, citalopram, paroxetine, fluvoxamine, escitalopram (lexapro), sertraline, venlafaxine, moclobemide, phenelzine, duloxetine and tranylcypromine.

According to a preferred embodiment of this aspect of the present invention, the antidepressant is nortriptyline or fluoxetine.

Examples of anti-epileptic drugs include, but are not limited to, carbamazepine, valproate (valproic acid), ethosuximide and phenyloin.

Additional psychotropic drugs that are known to exert pain relief are GABA agonists [Blackburn-Munro G., et al., Curr Pharm Des. 2005; 11(23):2961-76]. Hence, the first chemical moiety may alternatively be a GABA agonist. Examples of GABA agonists are described hereinbelow. Conjugates of two GABA agonists that are linked to one another have never been described hitherto.

As stated hereinabove, the psychotropic drug, according to the present invention, is covalently coupled to a second chemical moiety, which is an organic acid.

The phrase "organic acid" refers to a moiety, as defined herein, that is derived from an organic acid that includes a free carboxylic group.

The term "free carboxylic group" includes a "—C(=O)OH" group either as is, in its protonated or in its ionized or salt state.

The organic acid constituting the second moiety in the conjugates described according to the present invention, can be, for example, a moiety that has a general formula —R—C(=O)—, where R can be, for example, a hydrocarbon that has 1-20 carbon atoms.

The term "hydrocarbon" as used herein refers to an organic compound that includes, as its basic skeleton, a chain of carbon atoms and hydrogen atoms that are covalently linked therebetween.

Thus, the hydrocarbon according to the present invention can be, for example, alkyl or cycloalkyl.

As used herein, the term "alkyl" refers to a saturated aliphatic hydrocarbon including straight chain and branched chain groups. Preferably, the alkyl group has 1 to 20 carbon atoms.

Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, the alkyl has 3 to 5 carbon atoms.

As used herein, the term "cycloalkyl" includes an all-carbon monocyclic or fused ring (i.e., rings which share an adjacent pair of carbon atoms) group wherein one of more of the rings does not have a completely conjugated pi-electron system. Examples, without limitation, of cycloalkyl groups include cyclopropane, cyclobutane, cyclopentane, cyclopentene, cyclohexane, cyclohexadiene, cycloheptane, cycloheptatriene and adamantane.

The hydrocarbon, according to the present invention, can be straight or branched. The hydrocarbon can further be saturated or unsaturated. When unsaturated, the hydrocarbon can include a double bond or a triple bond in its carbon chain. An unsaturated hydrocarbon can further include an aryl.

As used herein, an "aryl" group refers to an all-carbon monocyclic or fused-ring polycyclic (i.e., rings which share adjacent pairs of carbon atoms) groups having a completely conjugated pi-electron system. Examples, without limitation, of aryl groups include phenyl, naphthalenyl and anthracenyl.

The hydrocarbon can further be substituted or non-substituted. When substituted, the substituent can be, for example, alkyl, cycloalkyl, aryl, heteroaryl, heteroalicyclic, hydroxy, alkoxy, aryloxy, cyano, halo, oxo, amido and amino.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups, include pyrrole, furane, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, cycloalkyl, hydroxy, alkoxy, aryloxy, cyano, halo, oxo, amido and amino.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, cycloalkyl, aryl, heteroaryl, halo, trihalomethyl, hydroxy, alkoxy, aryloxy, cyano, oxo, amido and amino.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

An "oxo" group refers to a —C(=O)—R' group, where R' can be, for example, alkyl, cycloalkyl or aryl.

A "halo" group refers to fluorine, chlorine, bromine or iodine.

A "trihalomethyl" group refers to a —CX$_3$— group wherein X is a halo group as defined herein.

An "amino" or "amine" group refers to a —NH$_2$ group.

An "amido" or "amide" group refers to a —C(=O)—NRaRb group, where Ra and Rb can be, for example, hydrogen, alkyl, cycloalkyl and aryl.

The hydrocarbon, according to the present invention, can further include one or more heteroatoms interspersed within its chain. The heteroatoms can be, for example, oxygen, nitrogen and/or sulfur.

The organic acid can further have a general formula —Z—C(=O)O—CHR$_2$—R$_3$, where Z can be, for example, a single bond, or a substituted or non-substituted hydrocarbon as described hereinabove; R$_2$ can be, for example, hydrogen or an alkyl having 1-10 carbon atoms; and R$_3$ can be, for example, hydrogen or a hydrocarbon as defined hereinabove.

Thus, representative examples of organic acids from which an organic acid moiety according to the present invention can be derived include oxalic acid, malonic acid, succinic acid, glutaric acid, maleic acid, fumaric acid, phthalic acid, isophthalic acid, tetraphthalic acid, butyric acid, 4-phenylbutyric acid, 4-aminobutyric acid (GABA), valeric acid, propionic acid, retinoic acid, acetyl salicylic acid and ibuprofen.

According to another embodiment of the present invention, the second chemical moiety of the chemical conjugates is a GABA agonist. Since, as mentioned hereinabove, GABA agonists alone have been shown to alleviate pain, conjugates containing such a moiety may release the GABA agonist in the brain and thus exert a dual, preferably synergistic, pain relief effect resulting from both the GABA agonist and the psychotropic drug.

As used herein, the phrase "GABA agonist" describes compounds that are capable of activating the GABA system in the brain; either directly or indirectly, including compounds that directly bind the GABA receptor or to any other receptor that affects the GABA system, and are therefore pharmacologically related to GABA. The term "GABA agonist" is hence understood to include GABA itself.

Thus, GABA agonists, according to the present invention, include, in addition to GABA (γ-aminobutyric acid) itself, other GABA agonist which can be covalently coupled to a psychotropic drug.

Examples of such GABA agonists include (±) baclofen, isonipecotic acid, γ-hydroxybutyric acid, aminooxyacetic acid, β-(4-chlorophenyl)-γ-aminobutyric acid, piperidine-4-sulfonic acid, 3-aminopropylphosphonous acid, 3-aminopropylphosphinic acid, 3-(aminopropyl)methylphosphinic acid, 1-(aminomethyl)cyclohexaneacetic acid (gabapentin), 4-amino-5-hexenoic acid (y-vinyl GABA, vigabatrin) and 3-(2-imidazolyl)-4-aminobutanoic acid.

The organic acid, according to the present invention, is selected so as to enhance the therapeutic effect induced by the psychotropic drug. In addition, the organic acid may be selected to reduce the side effects that could be induced by the psychotropic drug if administered alone.

The phrase "to enhance the therapeutic effect" as used herein refers to the enhancement of a pain alleviating activity of the conjugates of the present invention, which is higher than that of the psychotropic agent and/or the organic acid that form the conjugate, when administered per se. As is demonstrated in the Examples section that follows, such an enhanced therapeutic activity is typically characterized by reduced effective concentrations of the drug that are required to achieve a certain therapeutic activity, as compared to the effective concentrations of the non-conjugated psychotropic agent and/or the organic acid.

The phrase "side effects" as used herein refers to adverse symptoms that may develop as a result of administering to a subject a certain drug and particularly a psychotropic drug.

According to a preferred embodiment of the present invention, the second chemical moiety in the chemical conjugates of the present invention is covalently linked to the first chemical moiety via a bond such as, for example, a carboxylic ester bond, an oxyalkyl carboxylic ester bond, an amide bond or a thioester bond.

As used herein, the phrase "carboxylic ester bond" includes an "—O—C(=O)—" bond.

As used herein, the phrase "oxyalkyl carboxylic ester bond" includes an "O—R—O—C(=O)—" bond, where R is an alkyl, as defined hereinabove. Preferably R is methyl.

The phrase "amide bond" includes a "—NH—C(=O)—" bond.

The phrase "thioester bond" includes a "—S—C(=O)—" bond.

Such bonds are known to be hydrolizable by brain derived enzymes, such as esterases and amidases, and it is therefore assumed that the chemical conjugates of the present inventions act as prodrugs that are metabolized in the brain and thereby simultaneously release the psychotropic drug and the organic acid, thus, providing for advantageous co-pharmacokinetics for the psychotropic drug and the organic acid.

Alternatively, the second chemical moiety in the chemical conjugates of the present invention is covalently linked to the first chemical moiety via an imine bond.

As used herein, the term "imine bond" describes a —C=NH— bond. An imine bond is also known in the art as a "Schiff base".

Herein, the term "treating" includes abrogating, substantially inhibiting, slowing or reversing the progression of a pain or substantially preventing the onset of a pain.

The term "administering" as used herein refers to a method for bringing a chemical conjugate of the present invention into an area or a site in the brain that has an effect on pain.

The chemical conjugate of the present invention can be administered intraperitoneally. More preferably, it is administered orally.

The term "subject" refers to animals, typically mammals having a blood brain barrier, including human beings.

The term "therapeutically effective amount" refers to that amount of the chemical conjugate being administered which will relieve to some extent the sensation of pain.

Thus, for example a therapeutically effective amount of nortriptyline-GABA ranges between 0.05 mg/kg body and 20 mg/kg body, more preferably between 0.1 mg/kg body and 4 mg/kg body and most preferably between 0.2 mg/kg body and 1.0 mg/kg body. A therapeutically effective amount of fluoxetine-GABA ranges between 1 mg/kg body and 40 mg/kg body, more preferably between 5 mg/kg body and 40 mg/kg body and most preferably between 10 mg/kg body and 30 mg/kg body. Preferably, the therapeutically effective amount of the conjugates of the present invention is lower than that used by the parent compound to exert a similar effect.

According to an additional aspect of the present invention, the conjugates of the present invention are used to treat an addictive disorder. As used herein, the phrase "addictive disorder" refers to a disorder characterized by a collection of symptoms (i.e., a syndrome) that is caused by a pathological response to the ingestion of mood altering substances. The symptoms include euphoria, craving, loss of control, withdrawal and inability to abstain. Examples of addictive disorders include but are not limited to an eating disorder, an addiction to narcotics, alcoholism and smoking.

Antidepressants (e.g. nortriptyline) were shown to be effective in combination with transdermal nicotine in increasing smoking cessation rate with little effect on withdrawal symptoms [Prochazka et al., Arch Intern Med. 2004; 164: 2229-2233]. Therefore, the GABA conjugates of the present invention can also enhance this inherent therapeutic characteristic of an antidepressant.

Likewise, both antidepressants and anticonvulsants have been shown to be effective in the treatment of alcohol dependence [Williams S. American Family Physician, Nov. 1, 2005, Volume 72, Number 9]. Thus, the GABA conjugates of the present invention can also enhance this inherent aspect of antidepressants and anti-convulsants.

In addition, conjugates of the present invention may be used to treat other diseases or disorders which are effectively treated by antidepressants or anti-convulsants. For example, in a mouse model of sudden unexpected death syndrome, antidepressants were shown to decrease the incidence of respiratory arrest [Tupal, S. Epilepsia, 47 (1):21-26, 2006, Blackwell Publishing, Inc.C 2006 International League Against Epilepsy]. Thus, antidepressant-GABA conjugates as described herein may be used to prevent this side-effect of epilepsy.

According to another aspect of the present invention, there is provided a chemical conjugate comprising a first chemical moiety covalently linked to a second chemical moiety, wherein each of the chemical moieties is an independent GABA agonist. According to one embodiment of this aspect of the present invention, the chemical conjugate comprises two independent γ-aminobutyric acids (GABA) linked by an alkyloxy carboxylic ester bond.

These chemical conjugates may be synthesized following the general procedure described in U.S. Patent Application No. 20040242570 and WO 2005/092392. The synthesis of an exemplary conjugate according to this aspect of the present invention is described in Example 1 of the Examples section hereinbelow.

The conjugates according to this aspect of the present invention can be beneficially utilized for treating various CNS-associated diseases and disorders and are particularly beneficial for treating CNS-associated diseases and disorders that involve low levels of GABA in the brain. These include, for example, a pain disorder, a motion disorder such as Parkinson's, Multiple Sclerosis, action tremors and tardive dyskinesia, a dissociative disorder, a mood disorder such as panic, anxiety, depression, an addictive disorder, manic behavior, an affective disorder, a neurodegenerative disease or disorder such as Alzheimer's and a convulsive disorder such as epilepsy.

Hence, according to another aspect of the present invention, there is provided a method of treating a CNS disease or disorder, which is effected by administering to a subject in need thereof a therapeutically effective amount of a chemical conjugate as described in this context of the present invention.

Accordingly, these chemical conjugates can be used for preparing a medicament, whereby such a medicament is preferably for treating a CNS disease or disorder.

Representative examples of CNS diseases or disorders that can be beneficially treated with the conjugates described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, Multiple Sclerosis, Huntington's disease, action tremors and tardive dyskinesia, panic, anxiety, depression, alcoholism, insomnia and manic behavior, Alzheimer's and epilepsy.

In any of the methods described herein, the chemical conjugate can be administered either as is, or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of lactic acid.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the chemical conjugates of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the chemical conjugates can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the chemical conjugates for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The chemical conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions. Alternatively, the active ingredient may be in powder form for constitution with a suitable vehicle, e.g., sterile, pyrogen-free water, before use.

The chemical conjugates of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of chemical conjugate effective to prevent, alleviate or ameliorate pain.

Determination of a therapeutically effective amount is well within the capability of those skilled in the art, especially in light of the detailed disclosure provided herein.

For any chemical conjugate used in the methods of the invention, the therapeutically effective amount or dose can be estimated initially from activity assays in cell cultures and/or animals. For example, the effectiveness of the conjugates may be assayed on rats which have undergone an L5/L6 spinal nerve ligation surgical procedure. Specifically, left paraspinal muscles are dissected from the spinous processes at the levels of L4 through S2 of anaesthetized rats and their L5 and L6 spinal nerves are isolated. Each spinal nerve is tightly ligated with e.g. a 4-0 silk suture distal to the dorsal root ganglion. Following spinal nerve ligation, the wound is sutured, and the skin is closed. Ten to 14 days following spinal nerve ligation, the rats are typically placed in individual Plexiglas chambers on an elevated wire mesh where they are allowed to acclimate. Following the acclimation period, rats are tested for tactile allodynia by applying a series of calibrated von Frey filaments to the plantar aspect of the left hind paw ipsilateral to the site of nerve injury. The mean 50% withdrawal threshold (g) is determined [Li Y, Dorsi M J, Meyer R A, Belzberg A J. Pain. 2000; 85 (3):493-502]. Rats that display a predrug withdrawal threshold>4 g are generally not considered allodynic and are excluded from the study. Following determination of predrug withdrawal thresholds, rats may be treated with either conjugates of the present invention or vehicle, and effects on tactile allodynia are determined over time by measuring hind paw withdrawal thresholds for time intervals such as 30, 60, 90, and 120 min post-injection.

The conjugates of the present invention were also tested on rats or mice using the hot plate test or formalin test as described below in Examples 2, 3 and 5 respectively.

The conjugates of the present invention were also tested by analyzing their ability to prevent secretion of inflammatory cytokines as described in Example 6 hereinbelow.

For example, a dose can be formulated in animal models to achieve a circulating concentration range that includes the IC50 as determined by activity assays (e.g., the concentration of the test compound, which achieves a half-maximal inhibition of the proliferation activity). Such information can be used to more accurately determine useful doses in humans.

Toxicity and therapeutic efficacy of the chemical conjugates described herein can be determined by standard pharmaceutical procedures in experimental animals, e.g., by determining the IC50 and the LD50 (lethal dose causing death in 50% of the tested animals) for a subject compound.

The data obtained from these activity assays and animal studies can be used in formulating a range of dosage for use in human.

Side effects of the conjugates of the present invention at doses which are effective at alleviating pain may be assayed using standard assays known in the art. For example, in order to investigate the possible non-specific muscle relaxant or sedative effects of the conjugates of the present invention mice or rats may be treated with the conjugates of the present invention, and subsequently tested on a rota-rod for motility. This apparatus consists of a bar with a diameter of 3.5 cm mice and 7 cm for rats, subdivided into four compartments. The bar rotates at a constant speed of 0.5-22 revolutions per minute and the animals are evaluated for the time taken to fall from the bar. The animals may be selected 24 hours previously by eliminating those which do not remain on the bar for 60 seconds. Results are typically expressed as the length of time animals remain on the rota-rod bar.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the pain alleviating effects, termed the minimal effective concentration (MEC). The MEC will vary for each preparation, but can be estimated from in vitro and/or in vivo data, as described hereinabove. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the pain to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the pain, the manner of administration, the judgment of the prescribing physician, etc.

Compositions of the present invention may, if desired, be presented in a pack or dispenser device, such as a FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the chemical conjugates of the invention formulated in a compatible pharmaceutical carrier may also be prepared, placed in an appropriate container, and labeled for the treatment of pain. Compositions comprising conjugates of two GABA agonists may also be labeled for the treatment of other disorders e.g. motion disorders such as Parkinson's, Huntingdon's disease, Multiple Sclerosis, action tremors and tardive dyskinesia, dissociative disorders, mood disorders such as panic, anxiety, depression, alcoholism, insomnia and manic behavior, affective disorders, neurodegenerative diseases or disorders such as Alzheimer's and convulsive disorders such as epilepsy.

Hence, according to preferred embodiments of the present invention, the pharmaceutical compositions of the present invention are packaged in a packaging material and are identified in print, on or in the packaging material, for alleviating pain.

According to a further aspect of the present invention, there is provided an article-of-manufacture, which comprises a pharmaceutical composition as described hereinabove, being packaged in a packaging material and identified in print, in or on the packaging material for use in the treatment of pain, as described herein. The pharmaceutical composition includes a pharmaceutically acceptable carrier, as described herein and any of the chemical conjugates described herein.

According to yet a further aspect of the present invention, there is provided an article-of-manufacture, which comprises a pharmaceutical composition as described hereinabove, being packaged in a packaging material and identified in print, in or on the packaging material for use in the treatment of an addictive disorder, as described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of GABA Conjugates of Antidepressant and Antiepileptic Drugs

Synthesis of 2-Propyl-pentanoic acid (valproic acid) 4-aminobutyryloxymethyl ester hydrochloride (AN-216): To a solution of 2-propyl-pentanoic acid N-t-boc-4-amino-butyryloxymethyl ester (AN-217, prepared as described in WO 2005/092392, 1.7 grams, 4.7 mmol) in ethyl acetate, a solution of 4N HCl in ethyl acetate was added. The obtained mixture was stirred for 4 hours at room temperature, the solvent was thereafter evaporated and the residue was further dried under high vacuum. The residue was dissolved in ether, and addition of hexane lead to precipitation of the desired product AN-216 (0.75 gram, 62%) as an amorphous solid having a melting point of 35-37° C.

$^1$H-NMR (CD$_3$OD): δ=0.9 (t, J=7.1 Hz, 6H, two CH$_3$), 1.2-1.64 (m, 8H, two CH$_2$CH$_2$Me), 1.95 (q, J=7.5 Hz, 2H, CH$_2$CH$_2$CH$_2$), 2.4-2.5 (m, 1H, CHCO), 2.53 (t, J=7.2 Hz, 2H, CH$_2$CO), 2.99 (t, J=7.2 Hz, 2H, CH$_2$N), 5.77 (s, 2H, OCH$_2$O).

$^{13}$C-NMR (CD$_3$OD): δ=14.2 (two CH$_3$), 21.5 (two MeCH$_2$), 23.5 (CH$_2$CH$_2$CH$_2$), 31.3 (COCH$_2$), 35.5 (two CH$_2$CH), 39.9 (NCH$_2$), 46.2 (CH), 80.6 (OCH$_2$O), 172.5 (CH$_2$CO), 176.4 (CHCO$_2$).

MS (CI/NH$_3$): m/z (%)=260 (MH$^+$, 100).

Synthesis of N-(3-(4-(trifluoromethyl)phenoxy)-3-phenylpropyl)-4-amino-N-methylbutanamide Hydrochloride (AN-227)

tert-Butyl 3-(N-(3-(4-(Trifluoromethyl)phenoxy)-3-phenylpropyl)-N-methyl carbamoyl)propylcarbamate (AN-229) was prepared as described in WO 2005/092392. AN-229 (0.5 mmol) was added to a solution of HCl in EtOAc (35 ml) and the resulting mixture was stirred for 3 hours. The solvent was thereafter evaporated and the product, AN-227, was obtained in quantitative yield.

$^1$H NMR (300 MHz, CDCl$_3$): δ=1.9 (quint, J=7.25 Hz, 2H), 2.52 (t, J=6.9 Hz, 2H), 2.87 (m, t J=7.38 Hz, 2H, minor), 2.93 (s, 3H, NMe minor), 2.97 (t, J=7.13 Hz, 3H, NMe, major), 3.03 (s, 3H, major), 3.59-3.67 (m, 2H), 5.37 (dd, J=8.6, 4.18 Hz, 1H, major), 5.42 (dd, J=8.57, 4.12 Hz, 1H, minor), 6.99-7.05 (m, 2H), 7.24-7.49 (m, 7H) ppm.

$^{13}$C NMR (300 MHz, CDCl$_3$): δ=23.7 (major), 23.9 (minor), 30.9 (minor), 31.5 (major), 33.8 (minor), 36.1 (major), 37.1 (major), 37.9 (minor), 40.42, 46.3 (major), 47.5 (minor), 78.5 (minor), 79.4 (major), 117.2, 124.1, 127.3, 127.8, 129.0 (major), 129.2 (minor), 129.7, 129.9 ppm.

Synthesis of 10,11-Dihydro-5-(3-methylaminopropylidene)-5H-dibenzo[a,d][1,4]cycloheptene 4-Amino-N-butanamide Hydrochloride (AN-228)

tert-Butyl 3-(10,11-Dihydro-5H-dibenzo[a,d]cycloheptane-5-ylidene-N-methyl-1-propanamine-3-(methylcarbamoyl)propyl carbamate (AN-230) was prepared as described in WO 2005/092392. AN-230 (0.5 mmol) was added to a solution of HCl in EtOAc (35 ml) and the resulting mixture was stirred for 3 hours. The solvent was thereafter evaporated and the product was obtained in quantitative yield in the form of two rotamers.

$^1$H NMR (300 MHz, CDCl$_3$): δ=1.67 (t, J=6.9 Hz, 1H), 1.8 (t, J=7.07 Hz, 1H), 2.1-2.35 (m, 2H), 2.4 (q, J=6.7 Hz, 2H), 2.6-2.9 (m, 5H), 3.3-3.4 (m, 2H), 5.76 (dt, J=7.86, 7.76 Hz, 1H), 6.7-7.3 (m, 8H) ppm.

Synthesis of GABA oxymethylGABA (AN-214)

Preparation of 4-tert-Butoxycarbonylamino-butyric acid

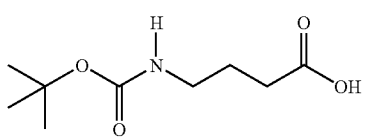

To a solution of γ-aminobutyric acid (1 equivalent) in t-BuOH (4 ml/gram) and H$_2$O (3 ml/gram) was added NaOH (1 equivalent), BOC$_2$O (1 equivalent), and the mixture was stirred at room temperature for 24 hours. The solvent was thereafter evaporated and the residue was partitioned between hexane and water. The aqueous layer was acidified with KHSO$_4$1N to reach pH=2, and was thereafter extracted with CH$_2$Cl$_2$. The organic layer was dried over MgSO$_4$ and the solvent was evaporated to give the desired product as a white solid (85% yield).

$^1$H-NMR (200 MHz) CDCl$_3$: δ=1.44 (s, 9H, t-Bu), 1.81 (quint, J=7.5 Hz, 2H, CH$_2$CH$_2$CH$_2$), 2.37 (t, J=7.5 Hz, 2H, CH$_2$CO$_2$), 3.17 (m, 2H, CH$_2$NH), 4.71 (bs, 1H, NH) ppm.

$^{13}$C-NMR (200 MHz) CDCl$_3$: δ=25.3 (CH$_2$CH$_2$CH$_2$), 28.4 (Me$_3$C), 31.1 (CH$_2$CO$_2$H), 39.7 (CH$_2$NH), 79.65 (CMe$_3$), 156.2 (NCO$_2$), 176.9 (CO$_2$H) ppm.

MS (CI/NH$_3$): m/z (%)=204 (MH$^+$, 24.3), 148 (MH$^+$—C$_4$H$_8$, 100), 130 (MH$^+$—C$_4$H$_{10}$O).

Preparation of 4-tert-Butoxycarbonylamino-butyric acid chloromethyl ester

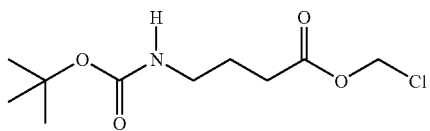 [SMILES: CC(C)(C)OC(=O)NCCCC(=O)OCCl]

To a mixture of chloromethyl chlorosulfate (1.1 equivalent) and 4-tert-Butoxycarbonylamino-butyric acid (1 equivalent) was added NaHCO$_3$ (3.6 equivalents) and Bu$_4$NHSO$_4$ (catalytic amount) in water/CH$_2$Cl$_2$ (1:1). The mixture was stirred at room temperature overnight. The organic phase was thereafter separated and the aqueous phase was extracted with CH$_2$Cl$_2$ (three times). The combined organic layer was washed with NaHCO$_3$ (×3), brine (×3), dried with MgSO$_4$, filtered and evaporated.

The product was purified by flash chromatography, using a 5:1 hexane:EtOAc as an eluent, and was isolated as a yellow oil (64% yield).

$^1$H-NMR (200 MHz) CDCl$_3$: δ=1.44 (s, 9H, t-Bu), 1.86 (quint, J=6.3 Hz, 2H, CH$_2$CH$_2$CH$_2$), 2.44 (t, J=6.93 Hz, 2H, CH$_2$CO$_2$), 3.18 (m, 2H, CH$_2$NH), 4.75 (bs, 1H, NH), 5.69 (s, 2H, CH$_2$Cl) ppm.

$^{13}$C-NMR (300 MHz) CDCl$_3$: δ=24.9 (CH$_2$CH$_2$CH$_2$), 28.3 (Me$_3$C), 31.1 (CH$_2$CO$_2$), 39.4 (CH$_2$NH), 68.6 (CH$_2$Cl), 79.2 (CMe$_3$), 155.9 (NCO$_2$), 171.3 (CO$_2$H) ppm.

MS (ES+): m/z (%)=274 (MNa$^+$, 40.6), 252 (MH$^+$, 40.2), 196 (MH$^+$—C$_4$H$_8$, 25.9).

Preparation of 4-tert-Butoxycarbonylamino-butyric acid 4-tert-butoxycarbonylamino-butyroloxymethyl ester

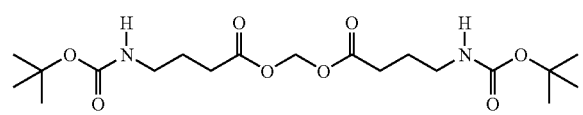 [SMILES: CC(C)(C)OC(=O)NCCCC(=O)OCOC(=O)CCCNC(=O)OC(C)(C)C]

A mixture of 4-tert-Butoxycarbonylamino-butyric acid (1.2 equivalents) and the chloromethyl ester described above (1 equivalent) in dry ethylmethylketone (EMK) was stirred under nitrogen atmosphere while triethylamine (1.2 equivalents) was added dropwise, and the reaction mixture was refluxed overnight. The formed white precipitate was thereafter filtered, washed with EtOAc and the filtrate was evaporated. The residue was dissolved in EtOAc and was washed with NaHCO$_3$ (×3), and brine (×3), dried with MgSO$_4$, filtered and evaporated. The crude product (brown oil) was purified by flash chromatography, using a 8:1 hexane:EtOAc mixture as eluent, to give the desired product as a yellow oil (38% yield).

$^1$H-NMR (200 MHz, CDCl$_3$): δ=1.44 (s, 18H, two t-Bu), 1.83 (quint, J=7.1 Hz, 4H, two CH$_2$CH$_2$CH$_2$), 2.41 (t, J=7.3 Hz, 4H, two CH$_2$CO$_2$), 3.16 (t, J=6.8 Hz, 4H, two CH$_2$NH), 4.67 (bs, 2H, two NH), 5.75 (s, 2H, OCH$_2$O) ppm.

$^{13}$C-NMR (300 MHz, CDCl$_3$): δ=25.0 (CH$_2$CH$_2$CH$_2$), 28.4 (Me$_3$C), 31.1 (CH$_2$CO$_2$), 39.7 (CH$_2$NH), 79.3 (OCH$_2$O), 155.9 (NCO$_2$), 172.9 (CO$_2$CH$_2$) ppm.

MS (ES+): m/z (%)=441 (MNa$^+$, 17.3), 319 (MH$^+$—BOC, 19), 196 (MH$^+$—BOC—C$_4$H$_8$, 25.9).

Preparation of 4-Amino-butyric acid 4-amino-butyryloxymethyl ester dihydrochloride (AN-214)

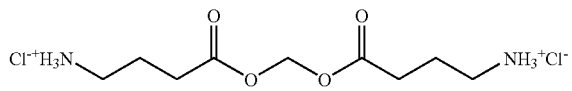

To a solution of the N-tert-Boc protected compound in EtOAc, a solution of 4N HCl in EtOAc was added. The reaction mixture was stirred for 4 hours at room temperature and the solvent was thereafter evaporated to give the crude product. The crude product was recrystallized from a MeOH-ether mixture, filtered and dried over P$_2$O$_5$ under vacuum to give the pure product as a white solid (90% yield).

mp: 155-158° C.

$^1$H-NMR (200 MHz, CD$_3$OD): δ=1.96 (quint, J=7.37 Hz, 4H, two CH$_2$CH$_2$CH$_2$), 2.55 (t, J=7.15 Hz, 4H, two CH$_2$CO$_2$), 2.99 (t, J=7.6 Hz, 4H, two CH$_2$NH), 5.76 (s, 2H, OCH$_2$O) ppm.

$^{13}$C-NMR (300 MHz, CD$_3$OD): δ=23.4 (CH$_2$CH$_2$CH$_2$), 31.3 (CH$_2$CO$_2$), 39.9 (CH$_2$NH$_2$), 80.8 (OCH$_2$O), 172.7 (CO$_2$CH$_2$).

MS (ES+): m/z (%)=219 (MH$^+$, 100), 242 (MNa$^+$, 90), 104 (MH$^+$—C$_5$H$_{10}$O$_2$N, 85) ppm.

Table 1 below presents the chemical conjugates synthesized by the methods described hereinabove.

Example 2

Effects of GAB-Antidepressant Drug and GABA-Anti-Epileptic Drug Conjugates as Determined by the Hot Plate Test Central pain perception was assessed by the analgesic response on a hot plate. The hot-plate test used to measure latency in response to heat was essentially carried out according to the method described by Eddy and Leimbach (1953), with the Materials and Methods Animals: Male Balb-c mice (8-14 weeks old) were obtained from Harlan, Israel. The mice were housed under conditions of controlled temperature (23±3° C.) and humidity (55±15%) with a 12 hour light/12 hour dark cycle. All experiments were carried out in accordance with the ethical guidelines of the International Association for the Study of Pain, and for the Committee on the Care and Use of Laboratory Animals of Tel Aviv University.

Experimental procedure: Nortriptyline (Sigma, Aldrich), fluoxetine, GABA (Sigma, Israel), the Nortriptyline-GABA conjugate (AN-228), the fluoxetine-GABA conjugate (AN-227) and valproyloxymethyl-GABA conjugate (AN-216) were solubilized in saline and administered to the mice by gastric gavage. After the indicated time periods, the animals were placed on a hot plate, (MRC, model-MH-4, 230 V/50 Hz, 750 W) which was maintained at 52±1° C. The time of response to the heat sensation was detected by one or more of the following reactions: raising paw, licking of the paw, jumping or running. Antinociception or analgesia reaction was measured as the latency to withdrawal evoked by exposing

TABLE 1

| | | |
|---|---|---|
| AN-214<br>GABA<br>oxymethylGABA | C$_9$H$_{20}$Cl$_2$N$_2$O$_4$<br>291.17 | ClH$_3$N〰〰C(O)O—CH$_2$—OC(O)〰〰NH$_3$Cl |
| AN-216<br>GABA-oxymethyl-<br>valproate | C$_{13}$H$_{26}$ClNO$_4$<br>295.80 | Me—CH(CH$_2$Me)—C(O)O—CH$_2$—OC(O)〰〰NH$_3^+$Cl$^-$ |
| AN-227<br>Flouxetine-GABA | C$_{21}$H$_{26}$ClF$_3$N$_2$O$_2$<br>430.16<br>C, 58.54; H,<br>6.08; Cl, 8.23;<br>F, 13.23; N,<br>6.50; O, 7.43 | F$_3$C—C$_6$H$_4$—O—CH(Ph)—CH$_2$—N(CH$_3$)—C(O)〰〰NH$_2$HCl |
| AN-228<br>Nortriptyline-<br>GABA | C$_{23}$H$_{29}$ClN$_2$O<br>384.2<br>C, 71.76; H,<br>7.59; Cl, 9.21;<br>N, 7.28; O, 4.16 | (dibenzosuberylidene)=CH—CH$_2$—N(CH$_3$)—C(O)〰〰NH$_3^+$Cl$^-$ | the mice paws to the thermal stimulus. Data was collected at the following time points: −60, 0, 120, 180, 240, and 300 minutes following administration of the drugs.

Statistical analysis: Data is expressed as mean±SD. The data was analyzed by the Student's t-test. Values of P<0.05 were considered statistically significant.

Experimental Results

Male Balb-c mice (6/group) were treated p.o. with the indicated doses of nortriptyline, respective equimolar doses nortriptyline-GABA conjugate or vehicle. Two hours later the animals were placed on the surface of the hot-plate (52±1° C.). Response to the heat, manifested by shaking or licking of the paws or jumping, was recorded as the index of response latency.

As illustrated in FIG. 1, 0.5 mg/kg of nortriptyline was significantly less effective two hours following administration than an equimolar dose of its GABA conjugate. At this dose, nortriptyline did not differ significantly (p>0.05) from control mice treated with vehicle only. At the dose of 4.5 mg/kg nortriptyline and equimolar dose of its GABA conjugate displayed a significant delay in the response compared to control mice treated with vehicle (p<0.05). These results demonstrate that the GABA-nortriptyline conjugate, imparted antinociceptive activity at a lower concentration than nortriptyline, demonstrating its advantage. Saturation in response by nortriptyline GABA was seen since equimolar dose of 0.5 mg/kg did not differ significantly from equimolar dose of 4.5 mg/kg.

A time course of the response to heat by mice treated with nortriptyline (0.25 mg/kg and 0.5 mg/kg) and an equimolar dose of nortriptyline-GABA (0.32 mg/kg and 0.64 mg/kg, respectively) is shown in FIGS. 2A-B. At a dose of 0.25 mg/kg, 4 hours following treatment, the analgesic effect of nortriptyline and its GABA conjugate increased significantly the latency of response compared to untreated mice (FIG. 2A). The conjugate exhibited significantly greater delay in response compared to the untreated mice at 4 and 6 hours post treatment and at 4 hours its antinociceptive effect was significantly greater than that of nortriptyline. This indicates that nortriptyline-GABA, compared to nortriptyline, is a more potent analgesic drug and its effect lasts longer. Two hours following a 0.5 mg/kg treatment, the conjugate caused a significant antinociceptive effect (compared to nortriptyline and vehicle treated mice) as illustrated in FIG. 2B. Un-conjugated Nortriptyline on the other hand, imparted a significant latency, (compared to vehicle treated animals), after 4 hours only. This indicates that not only does the additional GABA moiety increase the antinociceptive activity, but it also accelerates the onset of the protective effect.

The effect of repeated oral treatment with the drugs on response to heat was tested in mice (6/group) for nortriptyline (0.2 mg/kg) and its GABA conjugate (AN-228) at equimolar doses. The drugs were administered daily for 15 days and the treatment effect on heat sensation was measured trice a week. As illustrated in FIG. 3A, during the first week, the animals response to heat sensation prior to treatment (time 0), did not differ and was unaffected by the treatment. From the eighth day, a sustained latency response was noted prior to treatment and mostly in the nortriptyline-GABA conjugate and to a lesser extent in the nortriptyline treated mice. From the third day of treatment and during the five hours of testing (FIGS. 3B-E), typically, the conjugate imparted a significantly better antinociceptive effect compared to untreated animals or those treated with nortriptyline. A significantly improved antinociceptive effect compared to untreated animals and those treated with nortriptyline was observed 4 and 5 h after treatment with the daily dose from the first day of treatment. The results indicate that the nortriptyline-GABA conjugate produced a sustained and more effective analgesic response than nortriptyline. Repeated administration shortened the onset of the antinociceptive effect as well as increased the latency of the response.

The antinociceptive effects of the SSRI fluoxetine and its GABA conjugate (AN-227) were tested and compared in the hot-plate test. A time course of the response to heat by mice treated with fluoxetine (10 mg/kg) and equimolar dose of fluoxetine-GABA is shown in FIG. 4. At 2, 3 and 4 hours following treatment, the analgesic effect of fluoxetine-GABA conjugate on mice was significantly greater than that of untreated mice or mice treated with equimolar dose of GABA or fluoxetine. The observation indicates that fluoxetine-GABA, compared to fluoxetine, is a more potent analgesic and its effect lasts longer.

The effect of repeated treatment with fluoxetine and its GABA conjugate on response to heat was tested. Results are indicated in FIGS. 5A-E. Fluoxetine (10 mg/kg) and its conjugate at an equimolar dose were given orally to mice daily for 11 days and the treatment effect on heat sensation was tested at days 3, 7, 9 and 11. Delayed response to heat sensation in mice receiving fluoxetine-GABA was noted on days 3, 9 and 11 prior to treatment (FIG. 5A). A delay was noted only on day 11 with fluoxetine treated mice compared to vehicle treated animals. Typically during the 11 days of treatment, the GABA-fluoxetine conjugate exerted a significantly improved antinociceptive effect compared to fluoxetine or untreated animals. Fluoxetine treated mice also showed a significantly better antinociceptive effect compared to untreated animals. The results indicate that the fluoxetine-GABA conjugate produced a lasting and more effective analgesic response than fluoxetine.

Antiepileptic drugs, encompassing valproate and GABA and their analogs, have been shown to be effective analgesics. Since valproic acid crosses the BBB, a valproate-GABA conjugate could carry the GABA to the brain and the GABA in turn could potentiate the activity of valproic acid. 3, 4 and 5 hours following oral administration of 0.2 mg of valproyloxymethyl GABA, a significant latency in response to heat sensation compared to the untreated control mice, was observed as illustrated in FIG. 6. In parallel, GABA administered at >10-folds higher dose (2.39 mg/kg), had no activity.

A conjugate comprising two independent GABAs (AN-214) was also assayed for its pain relieving activities. Male Balb/c mice were treated orally for 5 consecutive days with either GABAoxymethylGABA (n=11), an equivalent molar dose of valproyloxyethyl GABA (n=11) or vehicle (n=8). As illustrated in FIG. 7, no antinociceptive activity was detected during the entire period.

Chronic administration of GABA neither had a cumulative effect on analgesia nor contributed to the antinociceptive effect as illustrated in FIG. 8. The mice were treated orally for 5 consecutive days with three different doses of GABA. No antinociceptive activity was detected during the entire period.

Example 3

Effects of GABA-Antidepressant Drug and GABA-Anti-Epileptic Drug Conjugates as Determined by the Formalin Test Intraplantar injection of formalin was used to assess the second, peripheral phase of pain.

Materials and Methods

Animals: Balb-c mice at 10 and 12 weeks of age were obtained from Harlan, Israel. Mice were housed under conditions of controlled temperature (23±3° C.) and humidity (55±15%) with a 12 hour light/12 hour dark cycle. All experiments were carried out in accordance with the ethical guidelines of the International Association for the Study of Pain, and for the Committee on the Care and Use of Laboratory Animals of Tel Aviv University.

Experimental Procedure (A) Fluoxetine: Five mice were used in each group and three hours following oral administration of either fluoxetine (10 or 30 mg/kg) or equimolar doses of the fluoxetine conjugate (AN-227), a 1% formalin solution was injected subcutaneously into the dorsal surface of the right hind paw.

(B) Nortriptyline: Eight mice were used in each group and three hours following oral administration of either nortriptyline (0.5 or 5 mg/kg) or equimolar doses of the nortriptyline conjugate (AN-228), a 1% formalin solution was injected subcutaneously into the dorsal surface of the right hind paw.

The formalin induced typical biphasic flinching behavior of the injected paw. The animals were returned to a glass chamber and the total time spent by the animal licking or biting the injected paw was counted. The frequency of pain-related behaviors was recorded during the early phase (0-5 min after injection) and the late phase (25-35 min after injection).

Experimental Results

As illustrated in FIGS. 9A-B, both doses of the fluoxetine conjugates of the present invention decreased significantly ($p<0.05$) the early neurogenic response to pain as compared to fluoxetine alone and the higher dose of the fluoxetine conjugate (equivalent to 30 mg/kg) reduced significantly ($p<0.05$) the late inflammatory peripheral response. As further illustrated in FIGS. 10A-B, both doses of the nortriptyline conjugates (equivalent of 0.5 and 5 mg/kg) of the present invention decreased significantly ($p<0.05$) the early neurogenic response and the late inflammatory peripheral response to pain as compared to nortriptyline alone.

Example 4

Effects of GABA-Fluoxetine Conjugate as Determined by the Carrageenan-Induced Paw Edema Test Intraplantar injection of carrageenan was used to assess the anti-inflammatory effects of GABA-fluoxetine conjugate (AN-227).

Materials and Methods

Experimental Procedure: Wistar rats (340-400 g) were marked with a permanent marker at the ankle of their left hind paws to define the area of the paw to be monitored. The rats were treated p.o. with fluoxetine 40 mg/kg (n=8) and an equimolar concentration of fluoxetine GABA (n=6) and control vehicle (n=8). After three hours, paw edema was induced by injecting 100 μl of a 1% solution of λ-carrageenan (Sigma, USA) in normal saline into the plantar surface of the left hind paw of the rats. The area of the induced edema was measured 2 and 4 hours later using caliper. The anti-inflammatory activity was expressed as area of edema calculated by the measured of its length and width (area=LXW).

Experimental Results

The fluoxetine-GABA conjugate of the present invention reduced edema both at two hours and four hours as compared to control and fluoxetine alone (FIG. 11). While 40 mg/kg of fluoxetine had no effect on reducing the inflammatory area, fluoxetine GABA conjugate significantly reduced the inflammatory area. Although in this animal model high doses of fluoxetine were previously shown to reduce oedema response in rats (Omar et al. Pharmacol. Res. 49 (2004) 119-131), the present example teaches that in side to side comparison, fluoxetine GABA conjugate acts at a lower dose.

Example 5

Effects of GABA-Nortriptyline Drug Conjugate Compared with Gabapentin and Nortriptyline as Determined by the Carrageenan-Induced Paw Edema Test and Hot Plate Test Intraplantar injection of carrageenan and the hot plate test was used to assess the anti-inflammatory effects of GABA-nortriptyline as compared to nortriptyline alone and to Gabapentin(1-(aminomethyl)cyclohexaneacetic acid).

Materials and Methods

Experimental Procedure: 12 week old Wistar rats, (250-300 g; Harlan, Israel) were divided in four groups (n=8-10) and treated as follows:
1. Control-vehicle
2. Nortriptyline 5 mg/kg, po. (14 mg+2.8 ml DDW)
3. Nortriptyline-GABA (AN-228), molarequivalent to 5 mg/kg, po, ((14.4 mg*1.28) 18.432 mg+2.8 ml DDW).
4. Gabapentin 100 mg/kg, po.

Wistar rats (250-300 g) were marked with a permanent marker at the ankle of their left hind paws to define the area of the paw to be monitored. The rats were treated as described herein above. After three hours, paw edema was induced by injecting 100 μl of a 1% solution of λ-carrageenan (Sigma, USA) in normal saline into the plantar surface of the left hind paw of the rats. The area of the induced edema was measured using caliper at the specified time points. The anti-inflammatory activity was measured by analyzing the increase in height.

The animals were also tested on hot-plate at −60, 0, 120, 240 min, 24 h and 48 hours.

Experimental Results

As illustrated in FIG. 12, a significantly delayed response to heat sensation was noted in rats receiving Nortriptyline-GABA as compared to Nortriptyline alone and Gabapentin 4 hours following injection.

As illustrated in FIG. 13A, paw height was significantly lower in rats having received Nortriptyline-GABA as compared to Nortriptyline alone and control at 4 hours, 24 hours and 48 hours following edema induction. As illustrated in FIG. 13B, paw height was significantly lower in rats having received Nortriptyline-GABA as compared to Nortriptyline alone, Gabapentin and control at 24 hours and 48 hours following edema induction.

Example 6

Effects of GABA-Nortriptyline Conjugate Compared with Gabapentin and Nortriptyline as Determined by Inflammatory Cytokine Secretion Cytokine secretion was used to assess the anti-inflammatory effects of GABA-nortriptyline (AN-228) as compared with nortriptyline alone or Gabapentin (1-(aminomethyl)cyclohexaneacetic acid).

Materials and Methods

Measurement of TNF-α and INF-γ in paw skin of mice: —Balb-c mice were divided to four groups (n=8). Two hours prior to formalin injection they were treated orally with 0.5 mg/kg nortriptyline, equimolar dose of AN-228 nortriptyline-GABA, a mixture of 0.5 mg/kg nortriptyline and equimolar dose of GABA, and 50 mg/kg gabapentin. After 4 hours the mice were sacrificed and tissues from the injection site were collected and analyzed for TNF-α or INF-γ. The collected tissues were homogenized in 300 µl of ice-cold PBS containing 0.4 mM NaCl, 0.05% Tween 20, 0.1 mM phenylmethylsulfonyl fluoride (PMSF) and 0.1 mM protease inhibitor cocktail (Calbiochem, Darmstadt, Germany). The homogenate was centrifuged 10,000 g for 30 min at 4° C. The supernatant was removed and assayed by the mouse TNF-α ELISA kit (BD OptEIA, CA, USA) and mouse INF-γ immunoassay (R&D Systems, Minneapolis, Minn., USA) according to the manufacturer's instruction. The results are expressed as ng TNF-α or INF-γ per mg protein).

Experimental Results

The amount of both INF-γ (FIG. 14A) and TNF-α (FIG. 14B) was significantly lower in mice treated with AN-228 Nortriptyline-GABA than in mice treated with an equimolar dose of Nortriptyline or an equimolar dose of Nortriptyline+GABA.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating pain, the method comprising administering to a subject in need thereof a therapeutically effective amount of a chemical conjugate which comprises nortriptyline covalently linked to γ-aminobutyric acid.

2. The method of claim 1, wherein said pain is selected from the group consisting of chronic pain and acute pain.

3. The method of claim 2, wherein said chronic pain is selected from the group consisting of neuropathic pain, visceral pain, fibromyalgia pain, inflammatory pain, headache pain, muscle pain and referred pain.

4. The method of claim 2, wherein said chronic pain is fibromyalgia pain.

* * * * *